(12) United States Patent
Kashkarov et al.

(10) Patent No.: US 10,368,972 B2
(45) Date of Patent: *Aug. 6, 2019

(54) EMBOLUS BLOOD CLOT FILTER WITH BIO-RESORBABLE COATED FILTER MEMBERS

(71) Applicant: C.R. BARD, INC., Murray Hill, NJ (US)

(72) Inventors: Alexander Germanovich Kashkarov, St. Petersburg (RU); Andrzej J. Chanduszko, Chandler, AZ (US)

(73) Assignee: C.R. BARD, INC., Murray Hill, NJ (US)

( * ) Notice: Subject to any disclaimer, the term of this patent is extended or adjusted under 35 U.S.C. 154(b) by 302 days.

This patent is subject to a terminal disclaimer.

(21) Appl. No.: 15/247,269

(22) Filed: Aug. 25, 2016

(65) Prior Publication Data

US 2017/0049550 A1    Feb. 23, 2017

Related U.S. Application Data

(63) Continuation of application No. 14/293,246, filed on Jun. 2, 2014, now Pat. No. 9,468,513, which is a
(Continued)

(51) Int. Cl.
*A61F 2/01* (2006.01)
*A61L 31/14* (2006.01)

(52) U.S. Cl.
CPC .............. *A61F 2/01* (2013.01); *A61L 31/148* (2013.01); *A61F 2002/016* (2013.01);
(Continued)

(58) Field of Classification Search
CPC .. A61F 2/01; A61F 2/013; A61F 2/848; A61F 2002/011; A61F 2002/015–018; A61F 2002/8483–8486
See application file for complete search history.

(56) References Cited

U.S. PATENT DOCUMENTS 6,176,871 B1 * 1/2001 Pathak ................ A61F 2/82
604/103.02
6,258,026 B1   7/2001 Ravenscroft et al.
(Continued)

OTHER PUBLICATIONS

International Preliminary Report on Patentability, dated Jul. 1, 2008.
(Continued)

*Primary Examiner* — Shaun L David
(74) *Attorney, Agent, or Firm* — Garvey, Smith & Nehrbass, Patent Attorneys, L.L.C.; Charles C. Garvey, Jr.; Seth M. Nehrbass

(57) ABSTRACT

A blood clot filter includes a number of locator members and anchor members, each of the members tipped with a retainer encompassed within bio-resorbable cover material. Upon delivery into a blood vessel, the locator and anchor members position the filter near the vessel centerline. After a period of time, the bio-resorbable cover material resorbs, allowing the retainer on the members to penetrate and attach to the vessel wall. A method of implanting the filter includes delivering the filter into a blood vessel and allowing the bio-resorbable cover material to resorb so retainers on the members can engage the vessel walls.

17 Claims, 18 Drawing Sheets

Related U.S. Application Data continuation of application No. 12/096,788, filed as application No. PCT/US2006/062730 on Dec. 29, 2006, now Pat. No. 8,777,975.

(60) Provisional application No. 60/754,597, filed on Dec. 30, 2005.

(52) U.S. Cl.
CPC . *A61F 2210/0004* (2013.01); *A61F 2230/005* (2013.01); *A61F 2230/008* (2013.01); *A61F 2230/0067* (2013.01)

(56) References Cited

U.S. PATENT DOCUMENTS

| | | | |
|---|---|---|---|
| 2001/0003796 A1 | 6/2001 | Yang et al. | |
| 2001/0039432 A1* | 11/2001 | Whitcher | A61F 2/01 606/200 |
| 2007/0100432 A1 | 5/2007 | Case et al. | |

OTHER PUBLICATIONS

Written Opinion of the International Searching Authority, dated Sep. 4, 2007.
International Search Report, International Publication No. WO 2007/079413, published Jul. 12, 2007.

\* cited by examiner

EMBOLUS BLOOD CLOT FILTER WITH BIO-RESORBABLE COATED FILTER MEMBERS

PRIORITY DATA AND INCORPORATION BY REFERENCE

This is a continuation of U.S. patent application Ser. No. 14/293,246, filed on Jun. 2, 2014, issued as U.S. Pat. No. 9,468,513 on Oct. 18, 2016, which is a continuation of U.S. patent application Ser. No. 12/096,788, filed on Dec. 29, 2006, issued as U.S. Pat. No. 8,777,975 on Jul. 15, 2014, which is a National Stage application under 35 U.S.C. 371 of International Application No. PCT/US2006/062730, filed Dec. 29, 2006, which claims the benefit of priority to U.S. Provisional Patent Application No. 60/754,597, entitled "Embolus Blood Clot Filter with Retainers on Locator Filter Members," filed Dec. 30, 2005 which is incorporated by reference in its entirety. This invention is related to the subject matter shown and described in the following: (i) PCT International Application No. PCT/US06/62722, filed Dec. 29, 2006, entitled "Removable Blood Clot Filter with Edge For Cutting Through the Endothelium" and claiming the benefit of priority to U.S. Provisional Patent Application No. 60/754,600, filed Dec. 30, 2005; (ii) PCT International Application No. PCT/US06/62719 filed Dec. 29, 2006, entitled "Embolus Blood Clot Filter with Post Delivery Actuation," and claiming the benefit of priority to U.S. Provisional Patent Application No. 60/754,633, filed Dec. 30, 2005; (iii) PCT International Application No. PCT/US06/62725, filed Dec. 29, 2006, entitled "Embolus Blood Clot Filter Delivery System," and claiming the benefit of priority to U.S. Provisional Patent Application No. 60/754,636, filed Dec. 30, 2005; (iv) PCT International Application No. PCT/US06/62720, filed Dec. 29, 2006, entitled "Embolus Blood Clot Filter with Floating Filter Basket," and claiming the benefit of priority to U.S. Provisional Patent Application No. 60/754,599, filed Dec. 30, 2005; and (v) PCT International Application No. PCT/US06/62733, filed Dec. 29, 2006, entitled "Embolus Blood Clot Filter Removal System and Method" and claiming the benefit of priority to U.S. Provisional Patent Application No. 60/754,598, filed Dec. 30, 2005, each of which is hereby incorporated by reference in its entirety.

TECHNICAL FIELD

This invention relates to a filter device that can be placed in a blood vessel to reduce the risk of embolisms. More particularly, this invention relates to a blood clot filter having anchoring and locating members in which at least one of the members has a portion covered with a bio-resorbable material to provide a delayed engagement between the member and a blood vessel wall.

BACKGROUND ART

In recent years, a number of medical devices have been designed which are adapted for compression into a small size to facilitate introduction into a vascular passageway and which are subsequently expandable into contact with the walls of the passageway. These devices include, among others, blood clot filters which expand and are held in position by engagement with the inner wall of a vein, such as the vena cava. Vena cava filters are known in the art as described, for example, in U.S. Pat. Nos. 4,425,908, 5,669,933 and 5,836,968, and European Patent Office publication 0 188 927 A2, each of which are incorporated by reference herein in their entirety. Such filters may include structure to anchor the filter in place within the vena cava, such as elongated diverging anchor members with hooked ends that penetrate the vessel wall and positively prevent longitudinal migration within the vessel. Such filters also may include locator structures to position the filter within the blood vessel, particularly with respect to the centerline of the vessel. Such locator structures may consist of a number of members which press against the walls of the vessel with approximately equal force, thus causing the center of the filter to move to the centerline of the vessel. A filter including anchor members having hooked ends and locator members is disclosed in U.S. Pat. No. 6,258,026, which is incorporated by reference herein in its entirety.

Referring to FIG. 20, a known expanded blood clot filter 10 is illustrated which is made from sets of elongated metal wires. The wires are held together at one end by a hub 12 where they may be plasma welded together and to the hub or otherwise joined. In one material phase, the wires, which are made of a shape memory material, can be straightened and held in a straight form that can pass through a length of fine plastic tubing with an internal diameter of approximately 2 mm (No. 7 French diameter catheter). At a defined temperature, the filter 10 recovers a preformed filtering shape as illustrated by FIG. 20. Similarly, wires of spring metal can be straightened and compressed within a catheter or tube and will diverge into the filter shape of FIG. 20 when the tube is removed. The blood filter 10 is typically delivered into a subject's blood vessel by being pushed out of a catheter positioned within the vein.

In its normal expanded configuration or preformed filtering shape, illustrated in FIG. 20, filter 10 is a double filter, having a first forwardly disposed filter basket 14 at the forward or leading end of the filter and a second forwardly disposed filter basket 16. The two filter baskets provide peripheral portions which can both engage the inner wall of a blood vessel at two longitudinally spaced locations, and the two filter baskets are generally symmetrical about a longitudinal axis passing through the hub 12.

The first filter basket 14 is formed by the anchor members 30, with up to twelve circumferentially spaced curved or linear wires forming the anchor members, which extend away from hub 12 and away from the longitudinal axis of the filter 10 and end in hooks 40, such as those illustrated in FIG. 21. The outwardly oriented hooks 40 generally lie on a circle at the maximum divergence of the anchor members 30. Six anchor members 30 are shown in FIG. 20. The anchor members may be of equal length, but normally the lengths differ so that the hooks 40 will fit within a catheter without becoming interconnected. The anchor members 30 may be much longer than the locators 20. In the expanded configuration shown in FIG. 20, the anchor members 30 are at a slight angle to the vessel wall, preferably within a range of from ten to forty-five degrees, while the hooks 40 penetrate the vessel wall to secure the filter against movement.

The second filter basket 16 is formed by locators 20 that extend angularly with respect to the longitudinal axis, outwardly and then downwardly from the hub 12 toward the forward end of the filter 10. As is shown in FIG. 20, each locator 20 may have a first locator section 21 which extends angularly out from the hub 12 to a shoulder 22, and an outer locator section 24 that extends angularly from the shoulder toward the forward end of the filter. Typically, there are six locators 20 of equal length extending radially outward from the hub 12 and circumferentially spaced, such as for example by sixty degrees of arc.

The anchors 30 may be radially offset relative to the locators 20 and may be positioned halfway between the locators 20 and also may be circumferentially spaced by sixty degrees of arc as shown in FIG. 22. Thus the combined filter baskets 14 and 16 can provide a wire positioned every thirty degrees of arc at the maximum divergence of the filter sections. With reference to the direction of blood flow, filter basket 14 forms a first concave opening toward the leading end of filter 10 and filter basket 16 forms a second concave opening toward the leading end of filter 10 downstream of filter basket 14.

For a filter to properly deploy the first and second filter baskets within the blood vessel, it is preferred that the filter hub 12 be positioned substantially along the centerline of the vessel. This centering function is performed by the locator members which have outer locator sections 24 that lie on a circle at their maximum divergence and engage the wall 17 of a vessel (preferably at an angle within a range of from ten to forty-five degrees) to center the hub 12 within the vessel. This is illustrated in FIG. 22. When positioned within a blood vessel, the locator members apply radial pressure to the walls, thereby pushing the filter hub 2 toward the vessel centerline. When a filter 10, such as that illustrated in FIG. 20, is ejected from an insertion catheter hub-end first, the locator members 20 will deploy first. Since the as-deployed radial separation between locator tips is larger than the diameter of the blood vessel, the locator tips contact and push against the walls of the blood vessel, as illustrated in FIG. 22, thereby centering the filter in the blood vessel before the anchor members deploy from the delivery catheter. In addition to serving as filter elements for catching blood clots, this centering function is an important function of the locator members.

Blood filters which use locator members as described above suffer from the disadvantage that the locator members do not contribute to anchoring the filter longitudinally in the blood vessel. This is because the locator members must be able to move with respect to the vessel wall while the filter centers in the blood vessel. If the locator members included hooks, they could hook into the vessel walls before the filter centers, leaving the filter in a cocked position. Accordingly, there is a need for a filter that includes hooks on locator members which hook into the vessel wall after the filter is centered in the blood vessel.

SUMMARY OF THE INVENTION

The various embodiments provide a blood filter that includes locator members with a retainer member disposed thereon. In order to permit the locator members to reposition the filter toward the centerline of the blood vessel during implantation, the retainers are covered or encompassed in a bio-resorbable material. The covered retainers are able to slide along the endothelial layer of the blood vessel as the filter moves to a centerline position. After the filter has been positioned in the blood vessel for a period of time, the bio-resorbable material covering the retainer is resorbed by the body, uncovering the retainers so that the retainers can engage the vessel walls, thereby helping to hold the filter in position within the vessel.

The various embodiments further provide a method of securing a blood filtering device within a blood vessel wherein a filter with retainer members covered by a bio-resorbable material position the filter near the centerline of the blood vessel. After a period of time, the bio-resorbable material is resorbed by the body, allowing the retainer members to engage vessel walls.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, explain features of the invention.

MODE(S) FOR CARRYING OUT THE INVENTION

The various embodiments will be described in detail with reference to the accompanying drawings. Wherever possible, the same reference numbers will be used throughout the drawings and this specification to refer to the same or like parts.

As used herein, the terms "about" or "approximately" for any numerical values or ranges indicates a suitable dimensional tolerance that allows the part or collection of components to function for its intended purpose as described herein. Also, as used herein, the terms "patient," "host" and "subject" refer to any human or animal subject and are not intended to limit the systems or methods to human use, although use of the subject invention in a human patient represents a preferred embodiment.

Figure 1A:
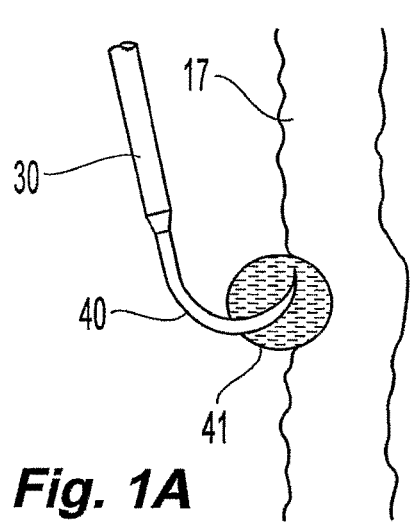
FIG. 1A is a cross sectional view of an anchor member covered with bio-resorbable material in place in a blood vessel.
Figure 1B:
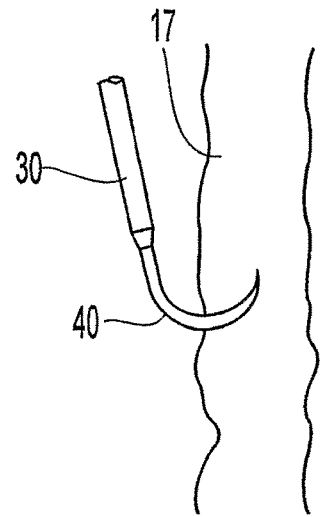
FIG. 1B is a cross sectional view of the anchor member shown in FIG. 1A after the bio-resorbable materials has resorbed.

In one preferred embodiment of a blood filter, locator members 20 are preferably tipped with a retainer such as, for example, a hook 40. The preferred locator members 20 can thus contribute to holding the filter in place within the blood vessel as well as locating the filter with respect to the body vessel, as illustrated in FIGS. 1A and 1B. In order to permit the hooked locator members 20 to move over the walls of the blood vessel 17 during the repositioning motion of aligning the filter near the blood vessel centerline, at least the tip portion of each retainer 40 is covered with a bio-resorbable material. The bio-resorbable material forms a smooth surface, or at least covers the point of the hook for a period of time until after the filter is centered in the vessel. Although a hook 40 is shown as a preferred embodiment of the retainer for the filter members, other forms of a retainer can be utilized to secure the members to the vessel wall such as, for example, a projection with a barb formed on the projection or a tip with two barbs formed proximate the tip.

Forming a blood clot filter of a Nitinol alloy material, such as Nitinol wire, can facilitate insertion of the filter into a delivery catheter and subsequent expansion of the filter within a vascular or other passageway. Although the filters of the various embodiments are preferably formed from a temperature responsive super-elastic shape memory material, such as Nitinol, they can also be formed of a compressible spring metal such as stainless steel or a suitable plastic.

As illustrated in FIG. 1A, the hook may be covered with a sufficient mass of bio-resorbable cover material 41 to encapsulate the tip of the retainer 40 and present a smooth surface for sliding along the inside of the vessel 17. Also, by having a larger surface area for contact with the vessel wall, as opposed to a point contact or line contact of the locator member, it is believed that the vessel will suffer less trauma as a result of filter placement. For further delayed uncovering of the retainer, a further coating or additional mass may be employed to postpone the complete dissolution of the cover material 41. Alternatively, a different, slower resorbing material may be used for the cover material 41.

Figure 1C:
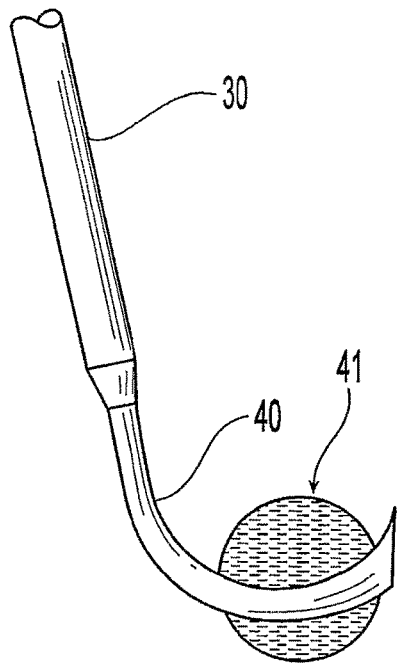
FIG. 1C is a cross sectional view of the sharp tip end of the hook of FIG. 1A being partially exposed.

In an alternative embodiment, as shown in FIG. 1C, the material 41 may cover only a portion of the retainer 40 while leaving a tip exposed. By having the tip exposed, the locating and anchoring functions can still be adequately achieved without employing the full anchoring ability of the retainer 40.

Figure 1D:
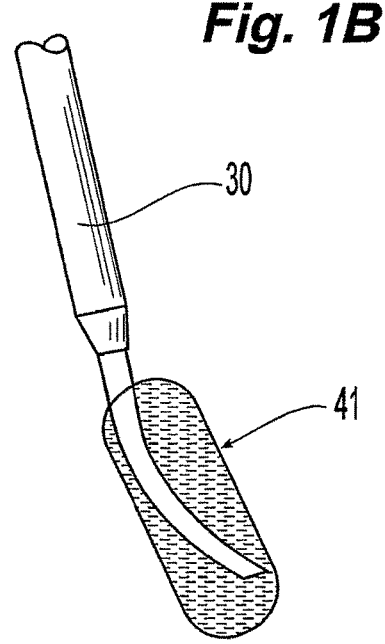
FIG. 1D is a cross sectional view of an anchor member in the form of a curved hook deformed into a straightened configuration and maintained in this configuration by an encapsulation material.

In a further alternative embodiment, the retainer 40 can be configured so as to provide positive engagement of the retainer to the vessel wall after an encapsulation material 41 has been resorbed. As shown in FIG. 1D, the retainer 40, which is in the form of a curved hook is deformed into a generally linear configuration and encapsulated in material 41 so as to maintain the hook in this deformed condition. As the material 41 is resorbed, the hook seeks out its original curved configuration. This reflex motion of the hook causes the hook to dig further into the vessel wall as more and more of the material 41 is resorbed. In another embodiment, instead of having the material 41 entirely covering the tip of the retainer, the material 41 can be a non-resorbable material that allows for creep of the non-resorbable material (e.g., polyurethane) under an internal stress provided by the deformed hook. By allowing for creep of the material, the deformed hook would tend to straighten over time so as to permit the exposed tip to penetrate through the polymer and into the vessel wall.

Figure 2:
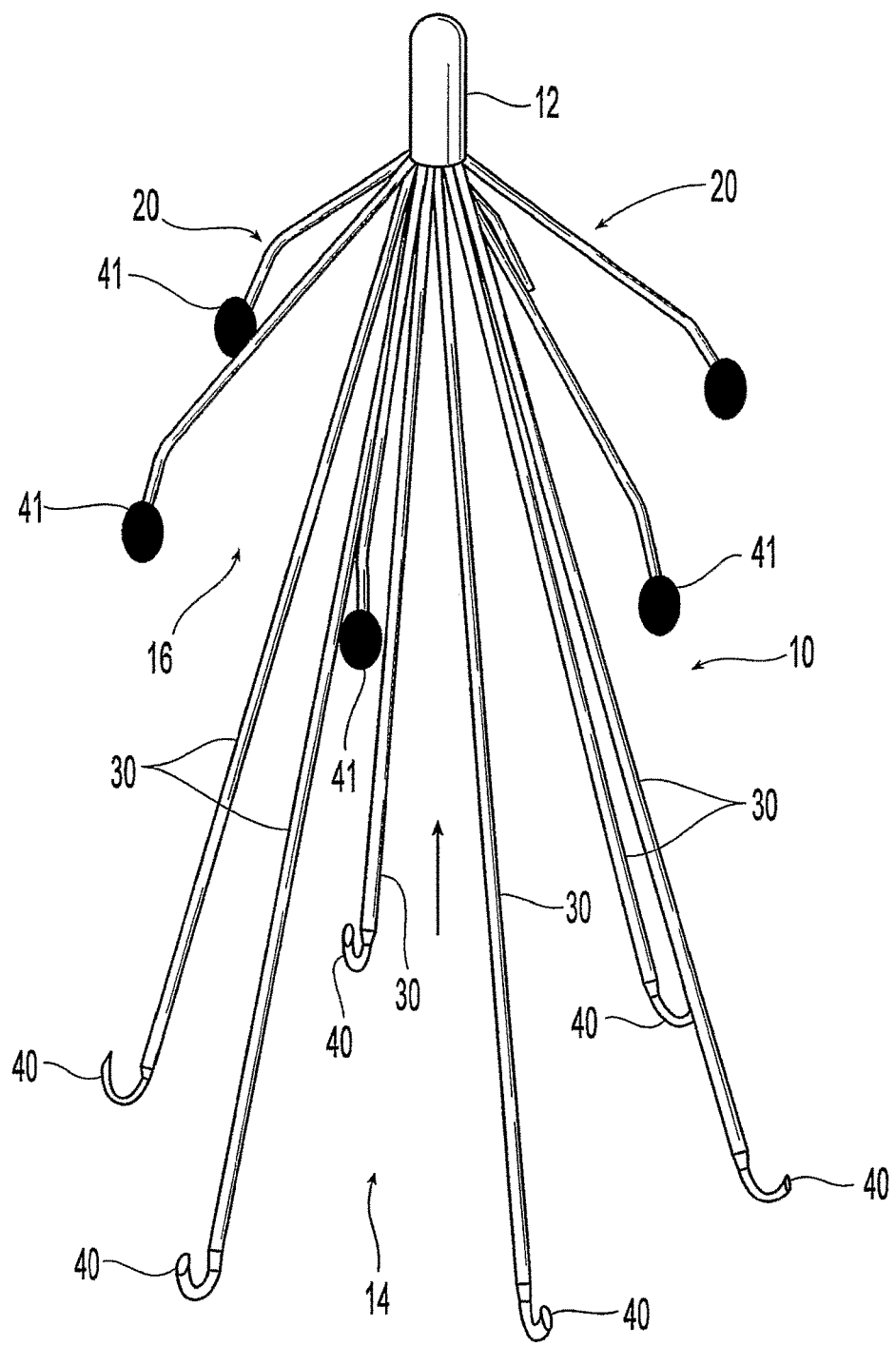
FIG. 2 is a side elevation view of an expanded blood clot filter according to an embodiment.

Referring to FIG. 2, a filter according to the various embodiments may have a configuration similar to that of conventional filters, as described above, with the addition of bio-resorbable cover material 41 positioned over retainers 40 on the locator members 20. Alternatively, conventionally covered locator members 20 not having a retainer member or hook can also be covered with a bio-resorbable material to delay direct engagement of the end of the locator member 20 with the blood vessel wall for a period of time, preferably until after the filter is centered in the vessel.

Figure 3A:
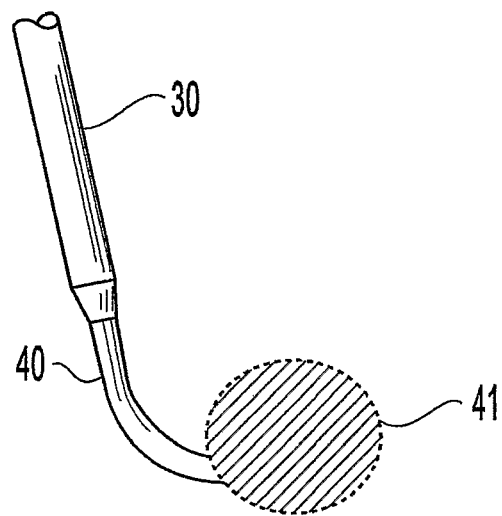
FIGS. 3A and 3B are side elevation views of a retainer for a member of the filter of FIG. 2 showing embodiments of the bio-resorbable material.
Figure 3B:
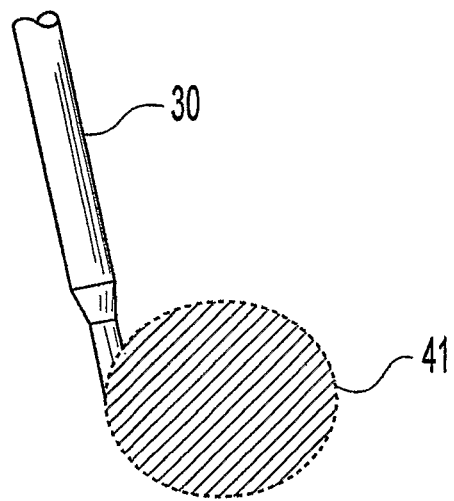

The amount of bio-resorbable material covering a retainer 40 may vary. As illustrated in FIG. 3A, the bio-resorbable cover 41 may encapsulate only the tip of the retainer, thereby preventing the tip from puncturing the blood vessel wall. In another embodiment illustrated in FIG. 3B, the bio-resorbable cover 41 may encompass a large fraction or all of the retainer 40. In either of the embodiments illustrated in FIGS. 3A and 3B, the cover material 41 may be a near solid bead. In an alternative embodiment, the cover material 41 may be in the form of a hollow sphere or bead, thereby encompassing at least a portion of the hook within a shell of bio-resorbable material. Use of a smaller bead, as illustrated in FIG. 3A, or a thin-walled hollow bead cover 41 may be considered for applications where relatively rapid uncovering of the retainer is desired. In such instances, the smaller amount of cover material will resorb faster than a larger and/or solid bead.

Figure 4:
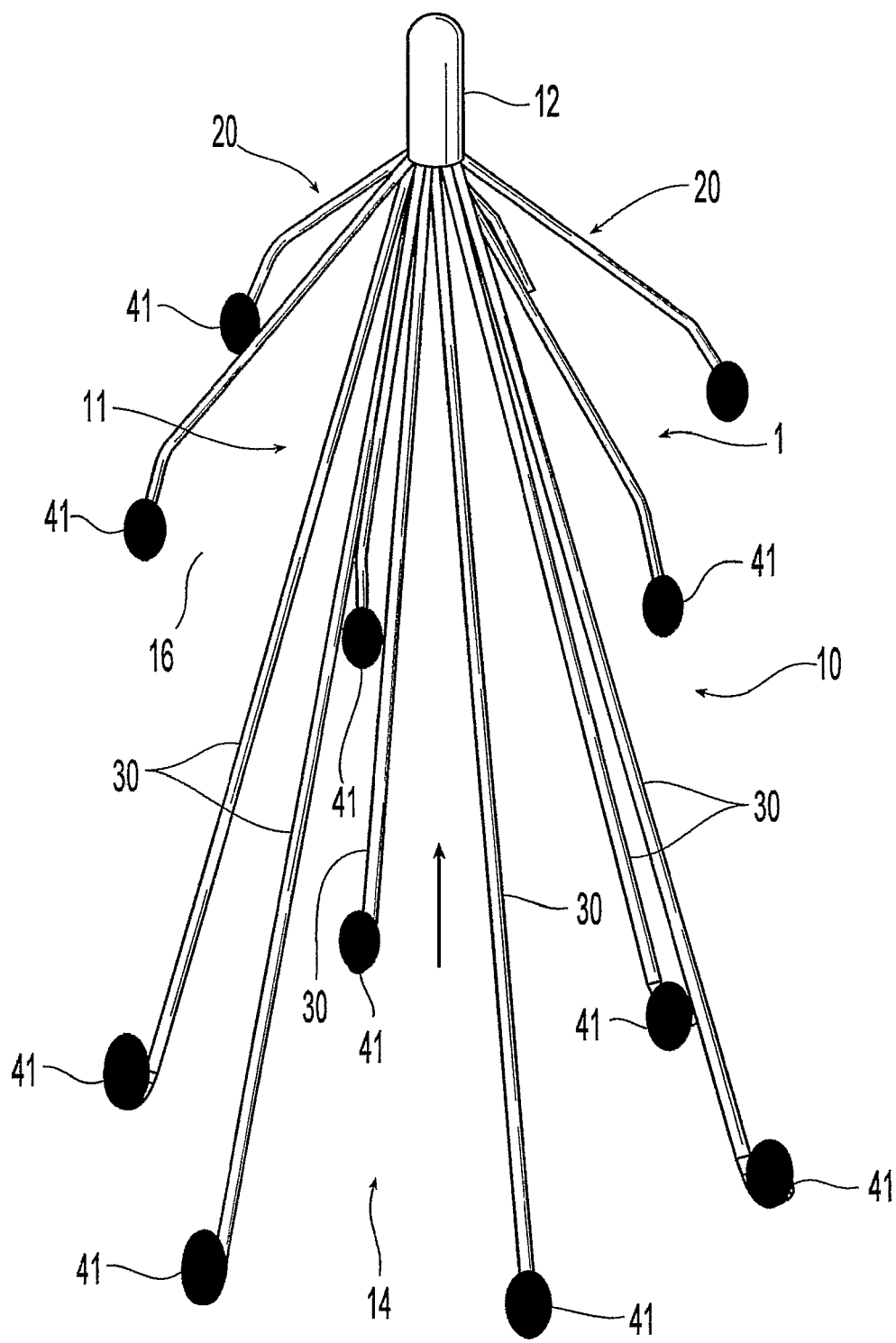
FIG. 4 is a side elevation view of an expanded blood clot filter according to another embodiment.
Figure 14:
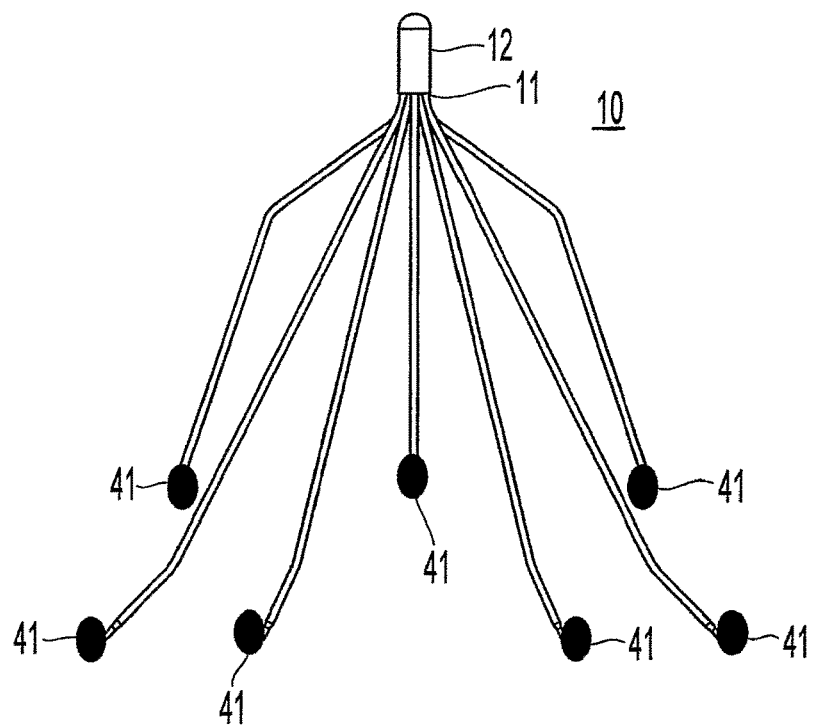
FIG. 14 is a side view of the filter of FIG. 5 after bio-resorbable material has been applied to the retainers on the locator members and anchor members.
Figure 15:
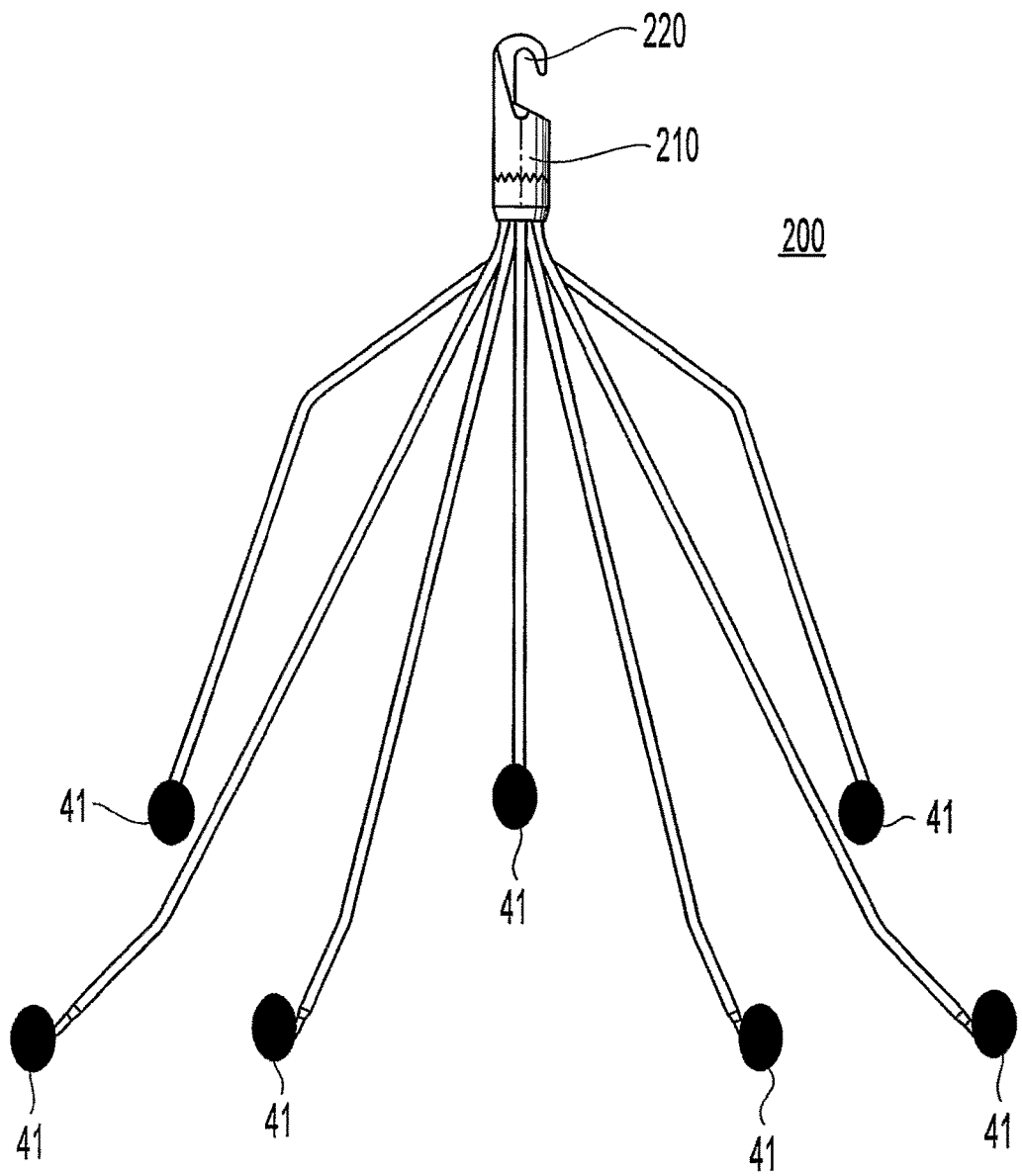
FIG. 15 illustrates another embodiment filter that includes a retrieving hook.

In yet another embodiment, the retainers 40 on the anchor members 30 may also be encompassed or covered with a bio-resorbable cover material 41 so that when the filter is first delivered into a blood vessel, the anchors deploy without driving the hooks 40 into the vessel wall 17. This embodiment may be employed on filters having locator members 20 with hooks, as illustrated in FIG. 4, or those without hooks. As with the previously described embodiment that comprises hooked locator members, after the filter has been in the blood vessel for a while, the cover material 41 is resorbed. When the material is resorbed, the anchor retainers 40 are uncovered and penetrate the vessel wall 17 to prevent the filter from being dislodged by blood flow. This embodiment has the advantage of allowing the filter to be immediately removed after delivery without damaging the endothelial layers of the blood vessel. Although FIGS. 4, 14 and 15 show all of the locator and anchor member retainers encapsulated, it is foreseeable that one could leave retainers 40 exposed to promote at least partial retention of the filter within the vessel immediately upon implantation.

Materials which break down or dissolve in blood and are assimilated by the body, i.e., resorbed, at predictable rates are well known in the medical arts and used in a variety of applications. For example, bio-resorbable sutures and staples are commonly used in surgical procedures to close internal wounds long enough to permit tissues to heal before being resorbed to reduce the potential for foreign object rejection and infections. A number of materials are used for bio-resorbable sutures and may be used for the bio-resorbable structures of the various embodiments. Such materials may be made from natural materials or synthetic polymers. Natural bio-resorbable materials include, but are not limited to, natural collagens, submucosa sheep intestine, plain gut serosa of beef intestine, and collagen beef flexor tendon. Natural absorbable materials prepared from mucosa or submucosal of sheep or beef intestines are broken down by enzymatic degradation within the cell. Synthetic bio-resorbable materials include, but are not limited to: Polyglycolic acid Dexon S homopolymer of glycolic acid; Polyglycolic acid Dexon plus homopolymer of glycolic acid coated with poloxamer 188; Polyglycolic acid Dexon II homopolymer of glycolic acid coated with potycaprolate; Polyglactine 910 Vicryl copolymer lactideglycolic acid coated with calcium stearate; Polydioxanone PDS polymer of paradioxanone; Polydioxanone PDS-II modified PDS; Polyglyconate Maxon copolymer of trimethylene carbonate and polyglycolicacid; and, Polyglecaprone 25 Monocryl copolymer of e-caprolactone and glycolide. Synthetic bio-resorbable materials are first hydrolyzed (hydrolytic degradation) and then metabolized by the cell. When the bio-resorbable material is degraded by hydrolysis the fragments are phagocytized by the enzymatic action of the cells, metabolized and excreted. The bio-resorbable materials can be configured to be absorbed or degraded within from 2 weeks to 2 years after implantation. Other materials can include biodegradable polymers such as polylactic acid, i.e., PLA, polyglycolic acid, i.e., PGA, polydioxanone, i.e., PDS, polyhydroxybutyrate, i.e., PHB, polyhydroxyvalerate, i.e., PHV and copolymers or a combination of PHB and PHV (available commercially as Biopol), polycaprolactone (available commercially as Capronor), polyanhydrides (aliphatic polyanhydrides in the back bone or side chains or aromatic polyanhydrides with benzene in the side chain), polyorthoesters, polyaminoacids (e.g., poly-L-lysine, polyglutamic acid), pseudo-polyaminoacids (e.g., with back bone of polyaminoacids altered), polycyanocrylates, or polyphosphazenes. As used herein, the term "bio-resorbable" includes a suitable bio-compatible material, mixture of materials or partial components of materials being degraded into other generally non-toxic materials by an agent present in biological tissue (i.e., being bio-degradable via a suitable mechanism, such as, for example, hydrolysis) or being removed by cellular activity (i.e., bioresorption, bioabsorption, or bioresorbable), by bulk or surface degradation (i.e., bioerosion such as, for example, by utilizing a water insoluble polymer that is soluble in water upon contact with biological tissue or fluid), or a combination of one or more of the bio-degradable, bio-erodable, or bio-resorbable materials noted above.

Two factors are believed to determine the rate of hydrolysis of synthetic bio-resorbable materials; the molecular weight and morphology of the polymer. Thus, by selecting among the available bio-resorbable materials and setting the thickness of the structure, the endurance of the bio-resorbable structure (i.e., the time in the body before the material fails under the loads applied by filter members) can be controlled. Additionally, hydrolytic degradation can be delayed by coating the surface of the bio-resorbable structure, such as with a hydrophobic layer formed of, for example, a copolymer of lactide, glactide and calcium stearate, which forms an absorbable, adherent, non-flaking lubricant which repels water and slows absorption, thereby improving retention of tensile strength. Additionally, the coating may be of a chemical structure that degrades, such as by breaking polymer chains to increase porosity, when exposed to sufficiently energetic radiation, such as ultraviolet light, or laser light of about 800 nanometers where the mammalian tissue is generally transparent to such wavelengths, so that the laser light can be used to degrade the coating without the need for an invasive procedure.

After a period of time, such as a few days to weeks, and typically less than 60 days, the bio-resorbable cover material 41 is sufficiently weakened by enzymatic or hydrolytic degradation that the tips of the retainers 40 will push through the cover material 41. With the tips uncovered, the retainers 40 may begin penetrating the endothelial layer, becoming lodged in the vessel wall 17.

Figure 12:
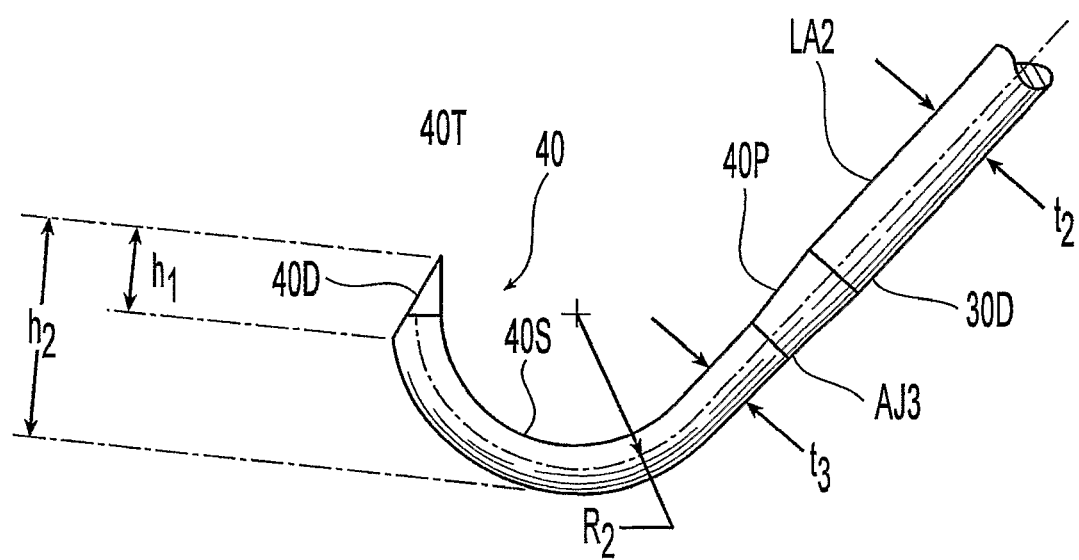
FIG. 12 is a close up side view of a hook of the anchor member for the filter of FIG. 5.

In a preferred embodiment illustrated in FIG. 12, the entire retainer 40 may be formed with a cross section throughout its length which is less than that of the anchor members 30 or locator members 20. The primary objective of the retainers 40 is to ensure that the filter does not migrate during normal respiratory function or in the event of a massive pulmonary embolism. The retainer thickness may be sized such that it is of sufficient stiffness when the anchor members 30 are expanded to permit the returner 40 to penetrate the blood vessel wall. However, when the filter is to be withdrawn from the vessel wall, withdrawal force in the direction of blood flow will cause flexure in the retainer so that the tip moves toward a position parallel with the axis A (i.e., the hook straightens). With the retainers so straightened, the filter can be withdrawn without tearing the vessel wall while leaving only small punctures. In one embodiment, the anchor member 30 preferably has a cross sectional area of about 0.00013 squared inches, and the retainer 40 has a cross sectional area preferably of about 0.000086 squared inches. Since Nitinol is also subject to stress sensitivity that can cause the material to undergo a phase transformation from the austenitic to the martensitic state while the temperature of the material remains above the transition temperature, the reduced cross section of the retainer 40 may transition to the martensitic state when subjected to a retraction stress, thus facilitating straightening. A preferred hook embodiment is shown and described in PCT International Application No. PCT/US06/017889, entitled "Removable Embolus Blood Clot Filter," filed May 9, 2006, which is incorporated by reference in its entirety herein.

In a further embodiment, a method of implanting a filter 10 in a blood vessel is provided. In this method, a clinician delivers a filter with retainers on its locator members covered with bio-resorbable material, as described herein, to a desired location in the blood vessel by pushing it through a catheter positioned in the vessel. The filter may be pushed through and out of the catheter by a push wire. Suitable delivery systems and methods are described, for example, in U.S. Pat. No. 6,258,026, which is incorporated by reference in its entirety herein, as well as in PCT International Application No. PCT/US06/17890, entitled "Embolus Blood Clot Filter and Delivery System," filed on May 9, 2006 which is also incorporated by reference in its entirety.

Once positioned in a blood vessel, the bio-resorbable material encapsulating the hooks is exposed to blood. After a period of time, exposure to blood leads to enzymatic or hydrolytic degradation of the bio-resorbable structure. Due to this degradation, the bio-resorbable material breaks down and is assimilated by the body, uncovering the hooks and allowing them to penetrate the walls of the blood vessel.

In the various embodiments, bio-resorbable material covers all or a portion of the retainers 40 until after the filter has been in the blood vessel for a predetermined period of time, thereby providing a means for delayed anchoring of at least a portion of the filter. This delayed anchoring (i.e. delayed retainer deployment) may be accomplished using any of the techniques described herein or their equivalents. The period of time for uncovering the hooks may be predetermined by adjusting the volume of bio-resorbable material over the retainer tips and/or by further coating the surface of the bio-resorbable material with a substance or material that resists water penetration for a period of time, thereby delaying onset of the resorption process.

Further control over the period of time after delivery that the hooks remain covered may be achieved using a suitable material that changes chemical structure upon exposure to a particular activating wavelength of radiation (e.g., UV or visible light). In one embodiment, the bio-resorbable cover material 41 is provided with a water repellant coating that prevents body fluids from degrading the resorbable material. Once exposed to the activating wavelength of radiation, the water repellant coating dissolves or becomes porous so that hydrolytic or enzymatic degradation of the underlying resorbable material can begin. In another example, exposure to a specific wavelength of light causes a light-activated material to change structure and thereby create separation between the cover material 41 and retainer 40. In an example, the activating radiation can be UV light, visible light or near infrared laser light at a wavelength (e.g., 800 nanometers) at which tissues are substantially transparent to such wavelength. In a particular embodiment, the coating material may be polyethylene with a melting point of about 60 degrees Celsius mixed with biocompatible dyes that absorb radiation in the 800 nm range, such as indocyanine green (which absorbs radiation around 800 nm and is biocompatible). Biocompatible dyes such as indocyanine green will absorb the light energy, thereby raising the temperature in the polymer to about 60 degrees Celsius or higher. When the melting point temperature, e.g., 60 degrees Celsius, is reached the polymer structurally weakens thereby causing the coating to lose integrity (i.e., crack, peal or otherwise become porous or at least a portion of the surface).

Several aspects of the various embodiments provide advantages over the known filters. For example, the capability of enabling locator members to also anchor the filter in a blood vessel is desirable, and the ability to immediately withdraw a filter from a patient without damaging the patient's blood vessels, since anchoring hooks are initially covered, may provide treatment advantages not available with known filters.

In addition to the foregoing embodiments, the bio-resorbable material covering all or a portion of the hooks may be employed with blood filters configured to be removable. An example of a removable filter embodiment is illustrated in FIG. 15. Further description of a removable filter is provided in PCT International Application No. PCT/US06/017889, entitled "Removable Embolus Blood Clot Filter".

Figure 5:
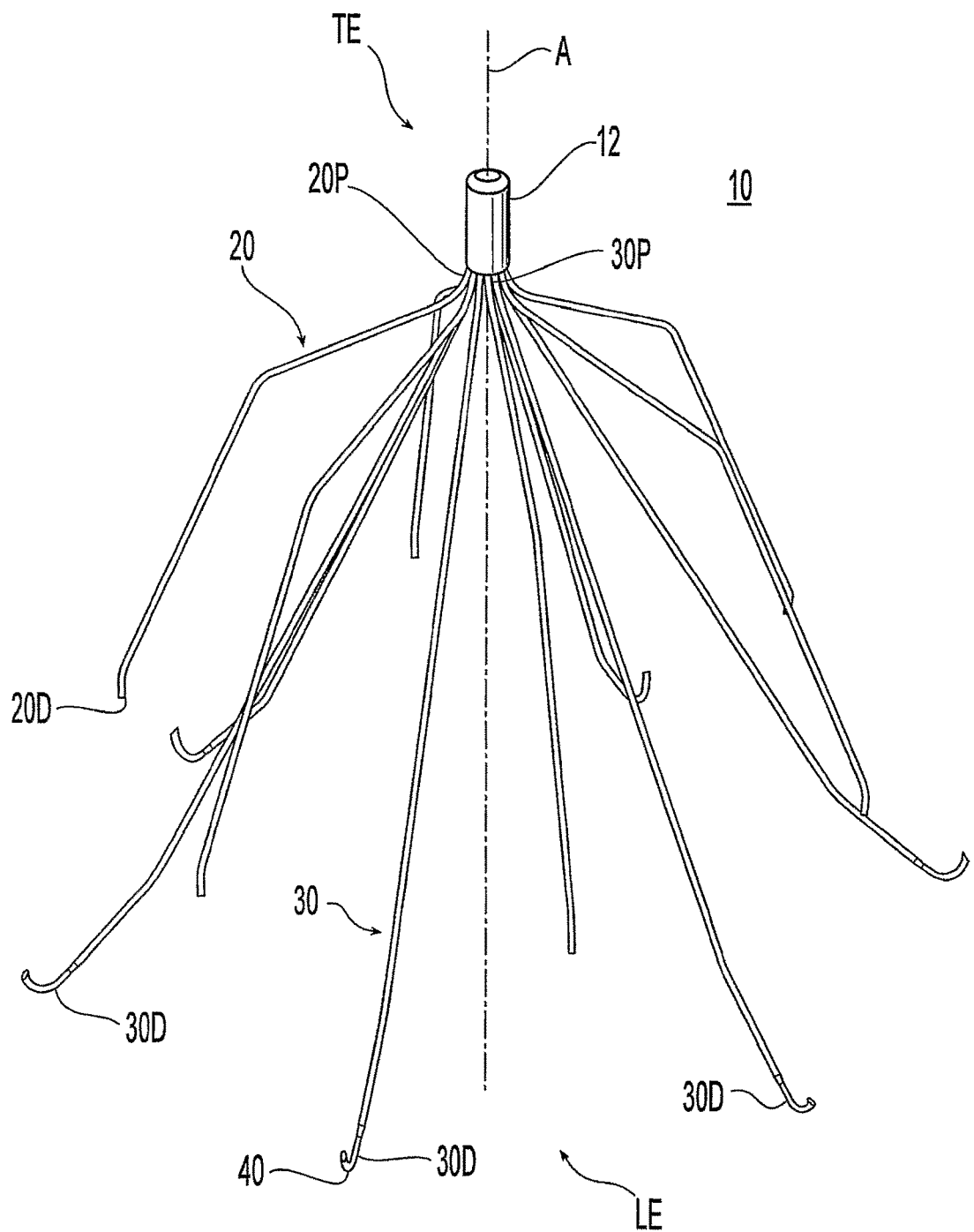
FIG. 5 is a top down perspective view of an embodiment of a removable blood filter before bio-resorbable material has been applied to the retainers.
Figure 6:
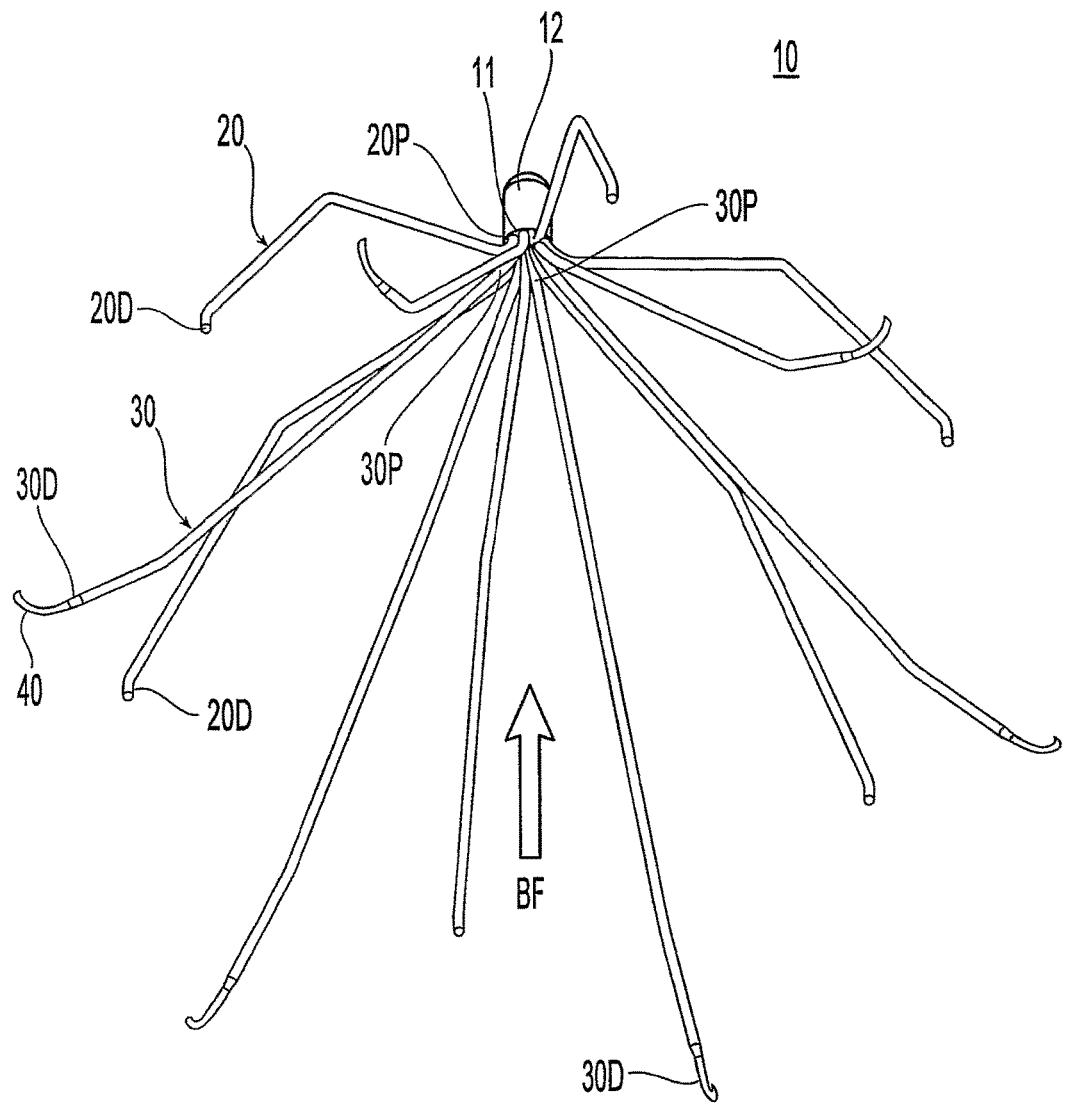
FIG. 6 is a bottom up perspective view of the embodiment of FIG. 5.
Figure 7:
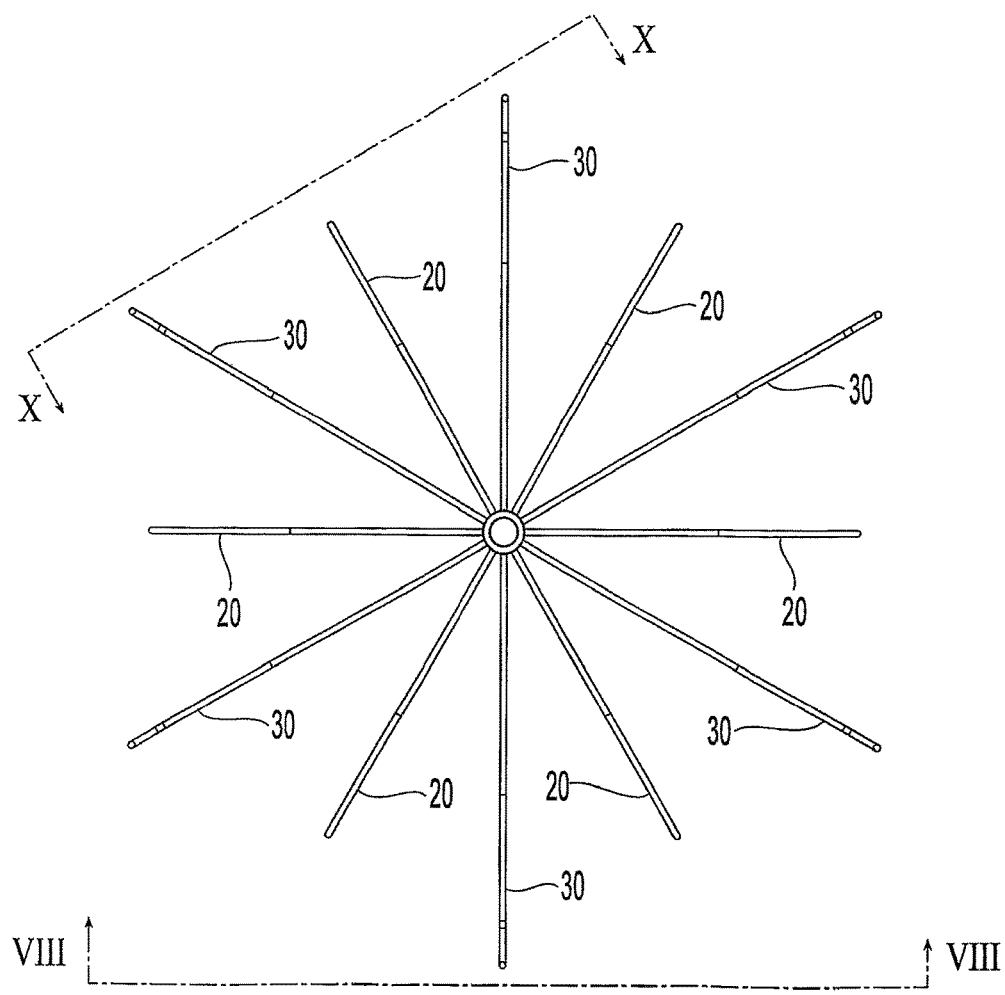
FIG. 7 is a plan view of the filter of FIG. 5 on longitudinal axis A.

Referring to FIG. 5, a filter 10 is illustrated in a perspective view. The filter 10 includes a hub 12, locator members 20, and anchor members 30 that have a hook 40. The filter 10 can be made from a plurality of elongate wires, which are preferably metal, such as, for example, Elgiloy® and more preferably a super-elastic shape memory alloy, such as Nitinol. The shape memory alloy can further be defined as preferably having an austenite finish ($A_f$) temperature below body temperature. The wires are joined at the filter trailing end by a hub 12 using a suitable connection technique, such as, for example, welding, laser welding, or plasma welding or being bonded together. Preferably, the wires are plasma welded. As used herein, "wire" refers to any elongated member of narrow cross section, including rods, bars, tubes, ribbon and narrow sections cut from thin plate, and is not intended to limit the scope of the invention to elongated members of circular cross section, cut from wire stock or manufactured according to a particular method of metal forming.

Each locator member 20 has a proximal locator end 20P and a distal locator end 20D. Similarly, each anchor member 30 has a proximal anchor end 30P and a distal anchor end 30D. The distal anchor end 30D may be provided with a hook 40, details of which are shown in FIG. 12.

Figure 8:
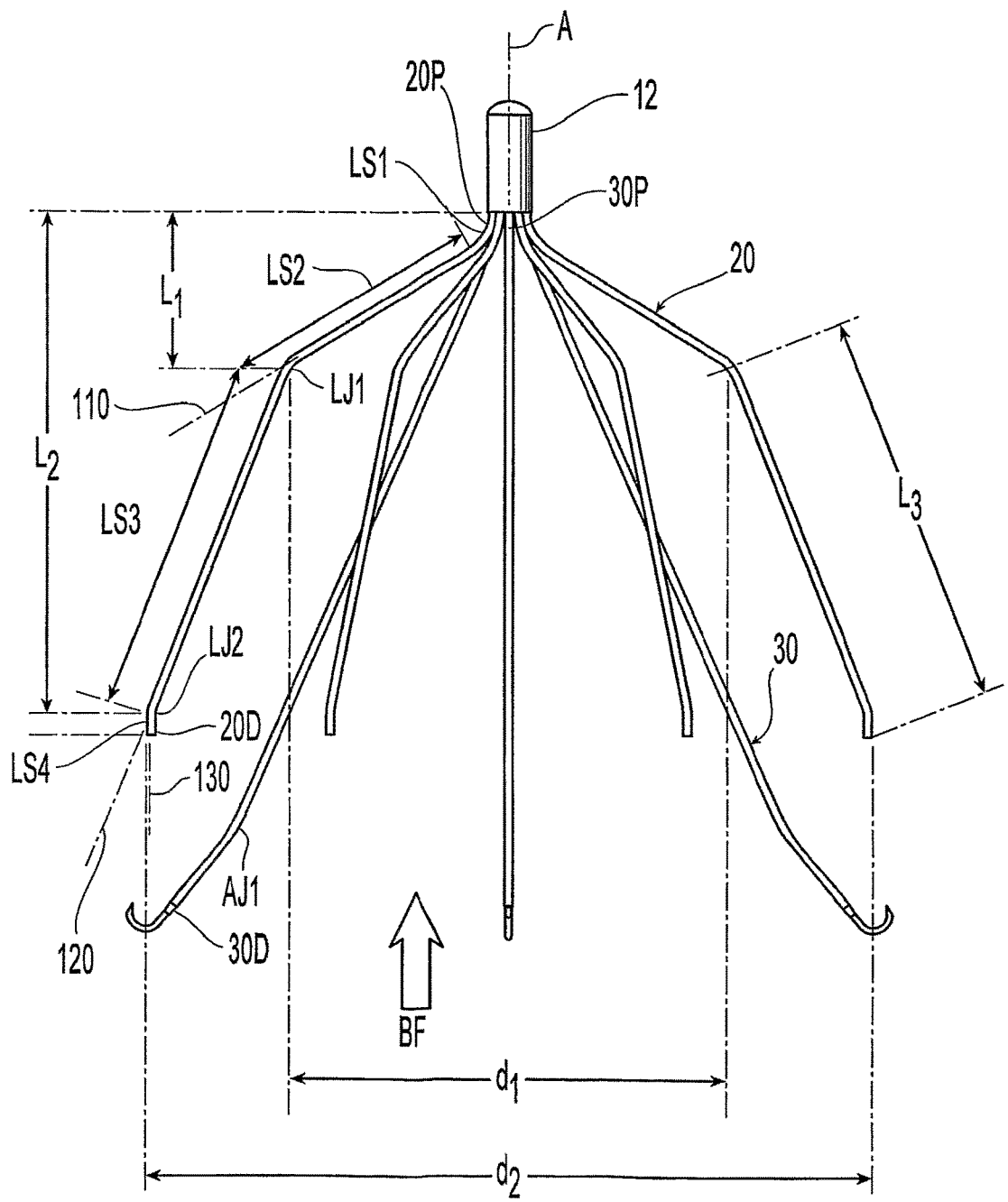
FIG. 8 is a side view of the filter of FIG. 5 viewed along axis VIII-VIII in FIG. 7.
Figure 9:
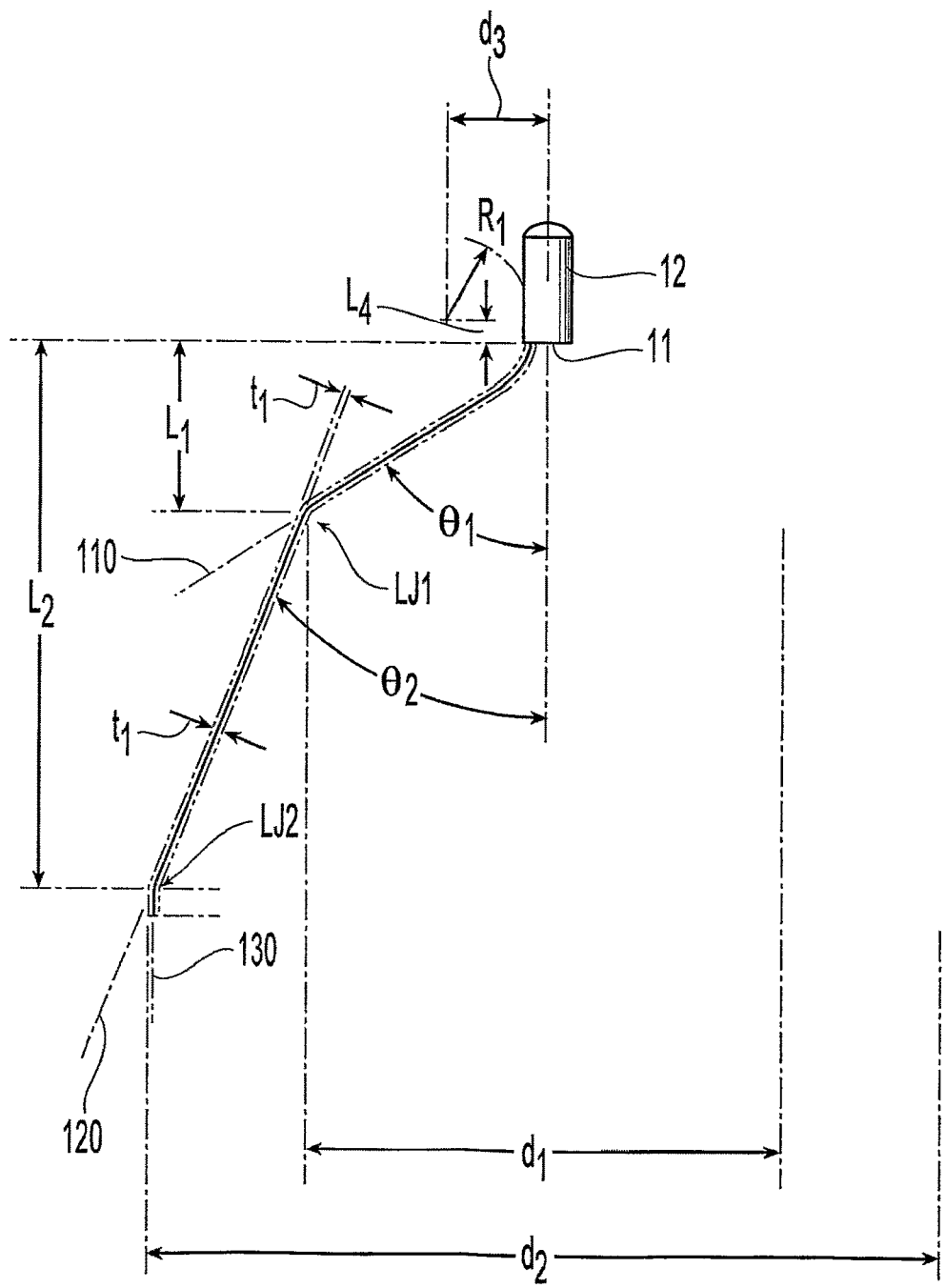
FIG. 9 is a side view of one locator member of the filter of FIG. 5.

Referring to FIGS. 8 and 9, the locator member 30 may be comprised of a plurality of locator segments, preferably between 3 and 6 segments and more preferably four locator segments LS1, LS2, LS3, and LS4. First locator segment LS1 may be a curved portion extending away from the hub 12 in a first direction along the longitudinal axis A. The second locator segment LS2 may extend generally linearly along a second axis 110; third locator segment LS3 extends generally linearly along a third axis 120; and the fourth locator segment LS4 extends generally linearly along a fourth axis 130 (or is configured as a hook as described below). In an embodiment, the various axes A, 110, 120, 130, and 140 are distinct from one another in that each may intersect with one another but none of them are substantially collinear with each other.

Figure 13:
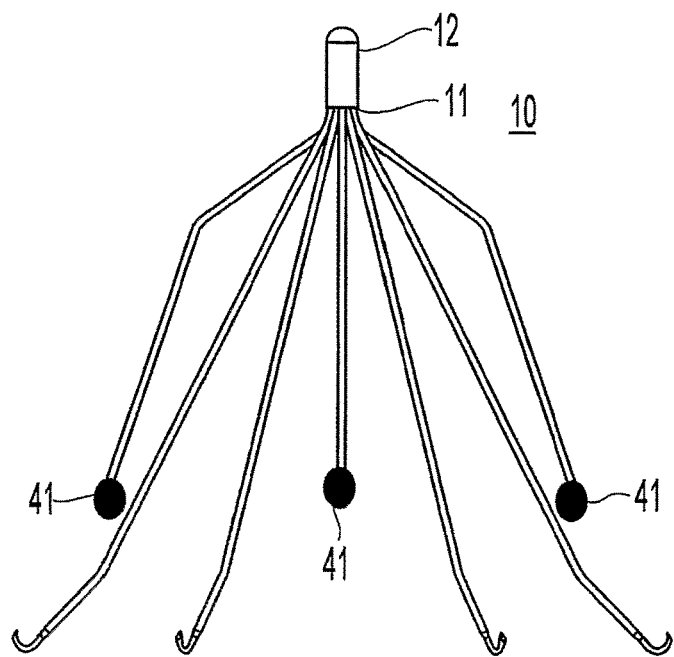
FIG. 13 is a side view of the filter of FIG. 5 after bio-resorbable material has been applied to the retainers on the locator members.

The locator segment LS2 may be distinct from locator segment LS3 by virtue of a joint or bend ill. The locator segment LS3 may be distinct from locator segment LS4 via a joint or bend LJ2. The joint or bend LJI or LJ2 can be viewed as a location formed by the intersection of the segments defining a radiused portion connecting any two segments. In one preferred embodiment, the locator member tip segment LS4 is configured as a hook for hooking into the endothelial layers of the blood vessel wall. Such hooks may be of the basic configuration illustrated in FIG. 12, or other configurations. As described above, embodiments featuring hooks on the locator members will include a bio-resorbable cover material 41, as illustrated in FIG. 13, to permit the locator members to glide easily over the endothelial layer during the initial positioning movements of the filter delivery procedure. As seen in FIGS. 1A, 1C, 2, 3A, 3B, 4, 13, 14, and 15, the bio-resorbable cover material 41 may have a rounded bead shape.

The number of locator members 20 may range from three to twelve locators. The filter embodiment illustrated in FIG. 8 includes six locators that are preferably generally equiangularly spaced about axis A. In the embodiment illustrated in FIG. 9, locator segment LS1 extends through an arc with a radius of curvature $R_1$ whose center may be located along an axis orthogonal to axis A over a radially transverse distance $d_3$ and over a longitudinal distance $L_4$ as measured from a terminal surface 11 of the hub 12 along an axis generally parallel to the longitudinal axis A. The locator segment LS2 extends along axis 110 to form a first angle $\theta_1$ with respect to the longitudinal axis A whereas the locator segment LS3 extends along axis 120 to form second angle $\theta_2$. As shown in FIG. 9, the first locator joint or bend LJ1 may be located at a longitudinal length $L_1$ generally parallel to axis A from the terminal surface 11. The first locator joint or bend LJ1 may be also located at a distance of about one-half distance $d_1$ from axis A on a generally orthogonal axis with respect to axis A as shown in FIG. 9, where the distance $d_1$ is the distance between inside facing surfaces of respective diametrically disposed locators 20. The second locator joint LJ2 may be located over a longitudinal length $L_2$ generally parallel to axis A. The second locator joint LJ2 may be located over a distance of about one-half diameter $d_2$ from axis A. The distance $d_2$ is the distance between the outermost surface of the fourth segment LS4 of respective diametrically disposed locators 20. The thickness of locator member 20 is $t_1$. Where the locator member 20 is preferably a wire of circular cross section, the thickness $t_1$ of the locator 20 may be the diameter of the wire.

A range of values may be used for the aforementioned dimensional parameters in order to provide locator members that will locate the filter within the vein or vessel in which the filter is to be applied in a manner that positions segment LS4 approximately parallel to the walls of the vein or vessel and provides sufficient lateral force against the vein or vessel wall for positioning but not so much force as to cause injury to the wall. In embodiments where the locator member tip segment LS4 is configured as a hook, the dimensional parameters will be set so as to apply sufficient force to the hooks to drive the tip into the vessel wall after the bioresorbable cover material 41 has been resorbed.

For example, a filter intended to be placed in a narrow vein or vessel, such as a human infant or canine vena cava, may have smaller dimensions $L_1$, $L_2$, $L_3$, $L_4$, LS1, LS2, LS3, LS4, $d_1$ and $d_2$ than a filter intended to be placed in a large vein or vessels, such as an adult human vena cava or femoral vein. Reducing these dimensions will facilitate complete deployment of the locator members so they can accomplish their intended positioning and filtering functions. In an example embodiment suitable for an adult human vena cava filter, when the filter is at the temperature of the subject and unconstrained, the radius of curvature $R_1$ is about 0.02 inches with the center of the radius $R_1$ being located over a distance $d_3$ from the axis A of about 0.1 inches and length $L_4$ of about 0.2 inches; the length $L_1$ may be about 0.3 inches; length $L_2$ may be about 0.9 inches; distance $d_1$ (as measured to the inside facing surfaces of diametrically disposed locators 20) may be about 0.8 inches; distance $d_2$ may be about 1.3 inches; the first angle $\theta_1$ may be about 58 degrees, the second angle $\theta_2$ may be about 22 degrees; and the thickness $t_1$ of the locator may be about 0.013 inches. It should be noted that the values given herein are approximate, representing a dimension within a range of suitable dimensions for the particular embodiment illustrated in the figures, and that any suitable values can be used as long as the values allow the filter to function as intended in a subject's blood vessel.

Figure 10:
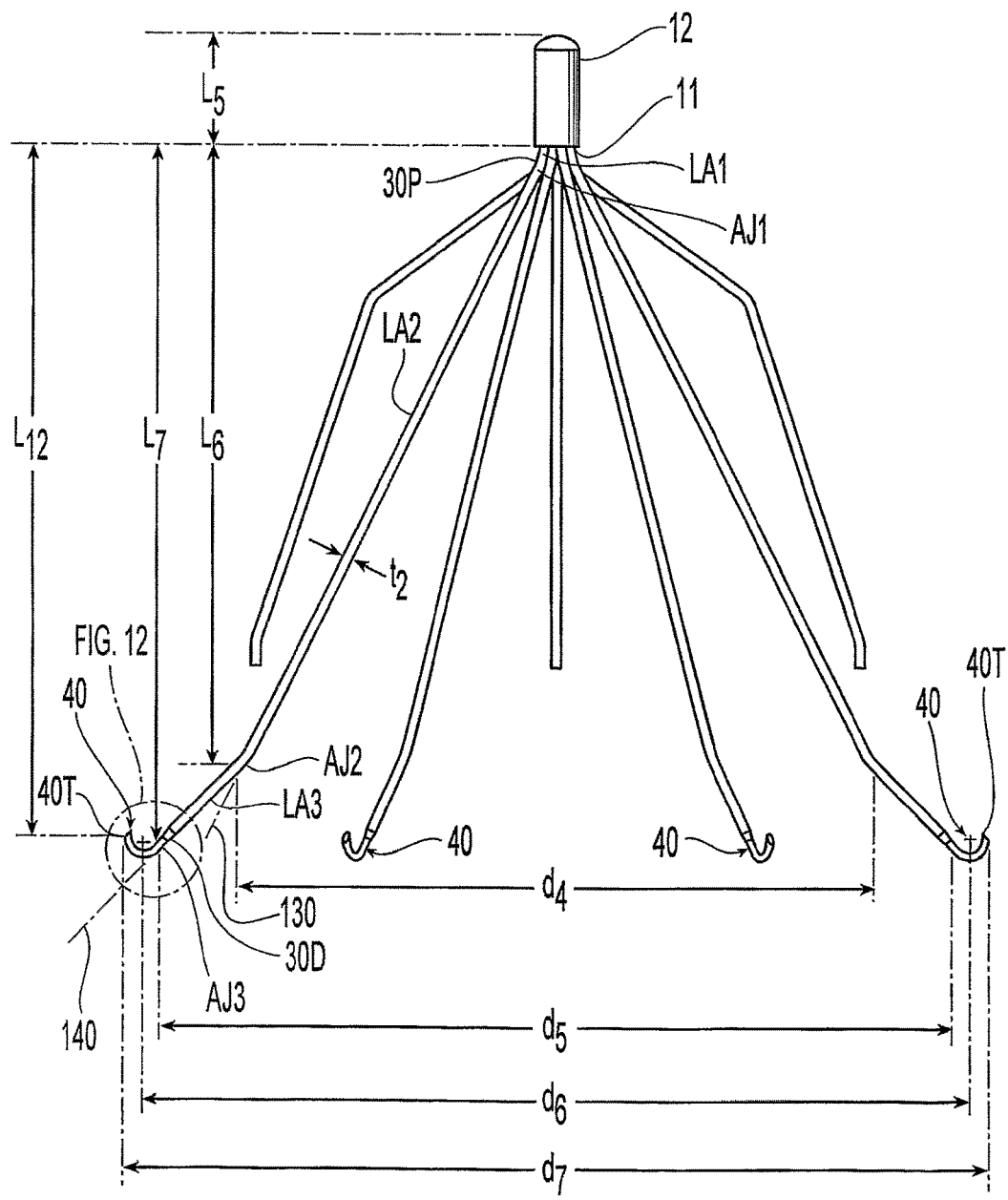
FIG. 10 is a side view of the filter of FIG. 5 viewed along axis X-X in FIG. 7.
Figure 11:
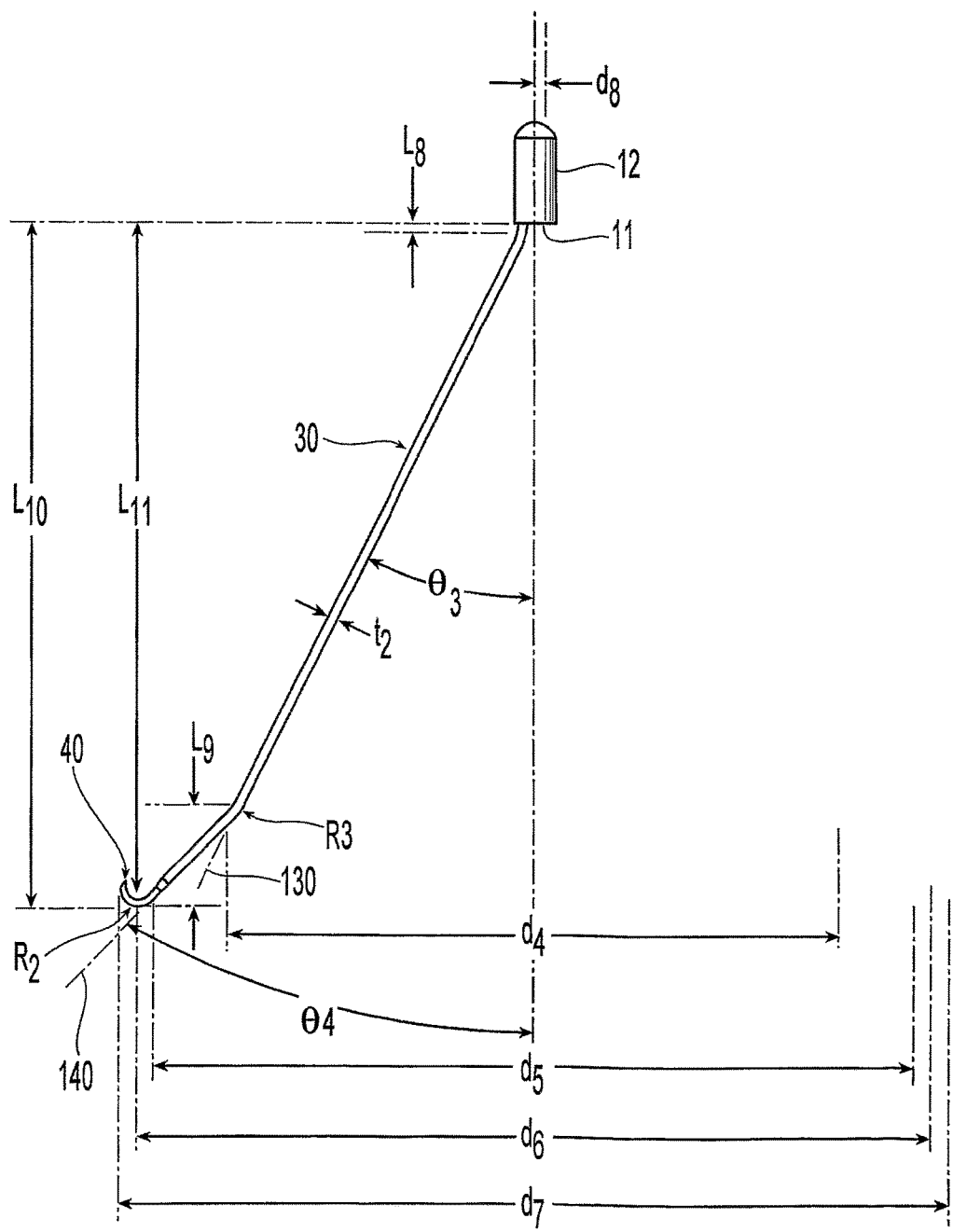
FIG. 11 is a side view of one anchor member of the filter of FIG. 5.

Referring to FIG. 11, the filter hub 12 may be provided with an internal cylindrical opening with a diameter of about two times the distance $d_8$. Referring now to FIG. 10 and FIG. 11, each of the plurality of anchor members 30 may be provided with a first anchor segment LA1, a portion of which is disposed within the hub 12, connected to a second anchor segment LA2 by a first anchor joint or bend AJ1, which may be connected to a third anchor segment LA3 via a second anchor joint or bend AJ2. The third anchor segment LA3 may be connected to the hook 40 via third anchor joint or bend AJ3. The first anchor segment LA1 preferably extends obliquely with respect to axis A. The second anchor segment LA2 preferably extends along axis 130 oblique with respect to the axis A over an angle $\theta_3$ with respect to the longitudinal axis A. The third anchor segment LA3 preferably extends along axis 140 oblique with respect to the longitudinal axis A over an angle $\theta_4$. The second anchor joint or bend AJ2 can be located at a sixth longitudinal distance $L_6$ as measured on an axis generally parallel to the axis A from the terminal surface 11 of the hub 12 and at about one half the fourth distance $d_4$ as measured between generally diametrical end points of two anchors 30 on an axis generally orthogonal to the axis A. The third anchor joint AJ3 may be located at a seventh longitudinal distance $L_7$ as measured along an axis generally parallel to axis A and at a transverse distance of about one-half distance $d_1$ as measured on an axis orthogonal to the axis A between the inner surfaces of two generally diametric anchors 30. The thickness of anchor member 30 is nominally $t_2$. Where, for example, the anchor member 30 is preferably a wire of circular cross section, the thickness $t_2$ of the anchor 30 may be the diameter of the wire. As shown in FIG. 11, the hook 40 may be contiguous to a plane located at a longitudinal distance $L_{10}$ as measured to the terminal surface 11 of hub 12. The hook 40 may be characterized by a radius of curvature $R_2$, in its expanded configuration at a suitable temperature, e.g., room temperature or the internal temperature of a subject. The center of the hook curvature $R_2$ can be located at a distance $L_{11}$ as measured along an axis generally parallel to the axis A from the terminal surface 11 of hub 12 and at one-half distance $d_6$ as measured between two generally diametrical hooks 40. The tips 40T of respective diametric hooks 40 may be located at longitudinal distance $L_{12}$ (which may be approximately the same as longitudinal distance $L_7$ to the third anchor joint AJ3) and at one half of distance $d_7$ between diametric hooks 40.

A range of values may be used for the aforementioned dimensional parameters in order to provide anchor members that will locate and anchor the filter within the vein or blood vessel in which the filter is to be applied in a manner that positions hooks 40 in contact with the walls of the vein or blood vessel and provides sufficient lateral force against the wall to ensure the hooks engage the wall (e.g., penetrating the endothelium) but not so much force as to cause injury to the wall. For example, a filter intended to be placed in a narrow vein or vessel, such as a child or dog vena cava, may have smaller dimensions than a filter intended to be placed in a large vein or vessels, such as an adult vena cava or femoral vein, so that the anchor members can deploy sufficiently to accomplish the positioning, anchoring and filtering functions. In an example embodiment suitable for an adult human vena cava filter, when the filter is at the temperature of the subject and unconstrained, the longitudinal distance or axial length $L_8$ of the first anchor segment LA1 may be about 0.02 inches; the longitudinal distance $L_9$ between the second and third anchor joints AJ2, AJ3 may be about 0.2 inches; $L_{10}$ may be about 1.4 inches; $L_{11}$ may be about 1.4 inches; $d_5$ may be about 1.5 inches; $d_7$ may be about 1.6 inches; $d_8$ may be about 0.01 inches; $d_6$ may be between 1.5 and 1.6 inches; $L_{12}$ may be about 1.4 inches; the radius of curvature $R_2$ may be about 0.03 inches; and the thickness $t_2$ of the anchor member may be about 0.013 inches. Most preferably, a very small radius of curvature $R_3$ characterizes anchor joint or bend AJ2 where $R_3$ may be about 0.01 inches.

Referring to FIG. 12, the hook 40 may be provided with a proximal hook portion 40P and a distal hook portion 40D on which a sharpened tip 40T is provided. The hook 40 may be formed to have a thickness $t_3$. Where the hook 40 is formed from a wire having a generally circular cross-section, the thickness $t_3$ may be generally equal to the outside diameter of the wire. In an embodiment, the hook thickness $t_3$ is approximately 0.8 that of the anchor thickness $t_2$. The wire may be configured to follow a radius of curvature $R_2$ whose center may be located at longitudinal distance $L_{11}$ and radial distance $d_6$ when the filter is at the temperature of a subject, as discussed above. The tip 40T may be provided with a generally planar surface 40D whose length may be approximately equal to length $h_1$. The planar surface length $h_1$ can be about 0.02 inches. The tip 40T may be located over a distance $h_2$ from a plane tangential to the curved portion 40S. The tip distance $h_2$ can be about 0.05 inches.

The material for the filter may be any suitable biocompatible material such as, for example, polymer, memory polymer, memory metal, thermal memory material, metal, metal alloy, or ceramics. Preferably, the material may be Elgiloy®, and most preferably Nitinol, which is a thermal shape memory alloy.

The use of a thermal shape memory material, such as Nitinol, for the locator and anchor members facilitates collapsing the filter radially inward from its normally expanded (i.e., unconstrained) configuration toward its longitudinal axis into a collapsed configuration for insertion into a body vessel.

Although the filters of the various embodiments are preferably formed from a temperature-responsive shape memory or super-elastic material, such as Nitinol, they can also be formed of a compressible spring metal such as stainless steel or a suitable plastic.

The structure of the hooks 40 is believed to be important in resisting migration of the filter once installed while allowing for removal from the blood vessel after installation. As in the case of hooks formed on the anchor members of known permanent vena cava filters, these hooks 40 penetrate the vessel wall when the filter 10 is expanded to anchor the filter in place and prevent filter migration longitudinally within the vessel in either direction. However when the hooks 40 are implanted and subsequently covered by the endothelium layer, they and the filter can be withdrawn without risk of significant injury or rupture to the vena cava. Minor injury to the vessel wall due to hook withdrawal such as damage to the endothelial layer or local vena cava wall puncture is acceptable.

To permit safe removal of the filter, the juncture section 40S may be considerably reduced in cross section relative to the thickness $t_2$ or cross section of the anchor member 30 and the remainder of the hook 40. The juncture section 40S may be sized such that it is of sufficient stiffness when the anchor members 30 are expanded to permit the hook 40 to penetrate the blood vessel wall. However, when the hook is to be withdrawn from the vessel wall, withdrawal force in the direction of blood flow BF will cause flexure in the juncture section 40S so that the hook tip 40T moves toward a position parallel with the axis A (i.e., the hook straightens). With the hooks generally straightened as such (but not quite fully), the filter can be withdrawn without tearing the vessel wall while leaving only small punctures. In one embodiment, the anchor member 30 has a cross sectional area of about 0.00013 squared inches, and the hook 40, particularly the curved juncture section 40S has a cross sectional area of about 0.000086 squared inches.

With reference to FIG. 12, it will be noted that the entire hook 40 can be formed with a cross section $t_3$ throughout its length that is less than that of the locator members 20 (which have thickness $t_1$) or anchor members 30 (which have thickness $t_2$). As a result, an axial withdrawal force will tend to straighten the hook 40. This elasticity in the hook structure prevents the hook from tearing the vessel wall during withdrawal. The force required to cause opening of the hooks 40 can be modulated to the total force required to resist filter migration. This is accomplished by changing the cross sectional area or geometry of the hooks, or by material selection, as discussed above.

By reducing the cross sectional area of a portion or all of the hooks 40 relative to that of the anchor members 30 or locator members 20, stress will be concentrated in the areas of reduced cross section when longitudinal force is applied to the hub 12 in the direction of blood flow BF (i.e., towards the hub 12 of the filter) such as to remove the filter. Under this concentrated stress, the reduced cross section portions of the hooks may transition to the martensitk state, thereby becoming elastic so that they straighten.

In an embodiment, each hook must be capable of resisting approximately at least 70 grams of force for the filter 10 to resist at least 50 mmHg pressure gradient in a 28 mm diameter vessel. To prevent excessive vessel trauma each individual hook needs to be relatively weak. By balancing the number hooks and the individual hook strength, minimal vessel injury can be achieved while still maintaining the at least 50 mmHg pressure gradient criteria, or some other predetermined pressure gradient criteria within a range of from about 10 mmHg to 150 mmHg.

In a further embodiment of the removable filter illustrated in FIG. 14, the hooks on the anchor members may also be encompassed or covered with a bio-resorbable cover material 41 so that when the filter is first delivered into a blood vessel, the anchors deploy without driving the hooks into the vessel wall. This embodiment may be employed on filters with locator members also having hooks, as illustrated in FIG. 14, and locator members without hooks. As with the previously described embodiments, after the filter has been in the blood vessel for a period of time, the cover material 41 is resorbed, thereby uncovering the anchor hooks, allowing them to penetrate the vessel wall to prevent the filter from being dislodged by blood flow. This embodiment has the advantage of allowing the filter to be removed within a predetermined period of time after delivery without damaging the endothelial layers of the blood vessel.

Instead of the hub 12 provided in the above described embodiments, a retrieving hook 220 can be provided as part of filter device 200, as in the embodiment shown in FIG. 15. The filter embodiment 200 preferably includes a hub 210 with a retrieving hook 220. Providing a retrieving hook 220 on the filter facilitates removal of the filter from a blood vessel, such as by means of a wire snare introduced through a removal catheter. Including the retrieval hook 220 on a filter whose retainers are covered by a bio-resorbable material 41, as illustrated in FIG. 15, permits a clinician to readily remove a filter soon after delivery without traumatizing the blood vessel. In this embodiment, the cover material 41 prevents the retainers, preferably configured as hooks, from engaging the blood vessel wall for a predetermined period of time and the retrieval hook 220 of the hub 210 facilitates capturing and retrieving the filter via a catheter. While FIG. 15 shows cover material 41 on both locator and anchor member hooks, the cover material may be applied only to the locator member hooks, or only to the anchor member hooks or to a combination of some locator hooks and some anchor member hooks as part of this embodiment.

Figure 16:
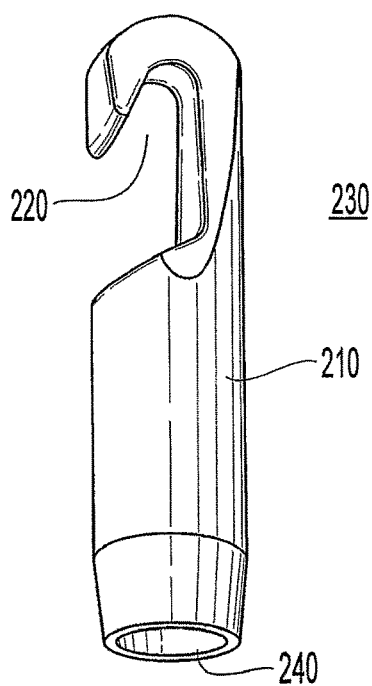
FIGS. 16-19 are detail views of a retrieving hook according to the filter embodiment of FIG. 15.
Figure 17:
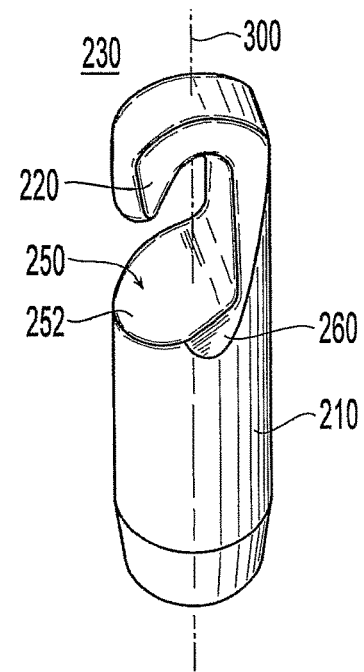
Figure 18:
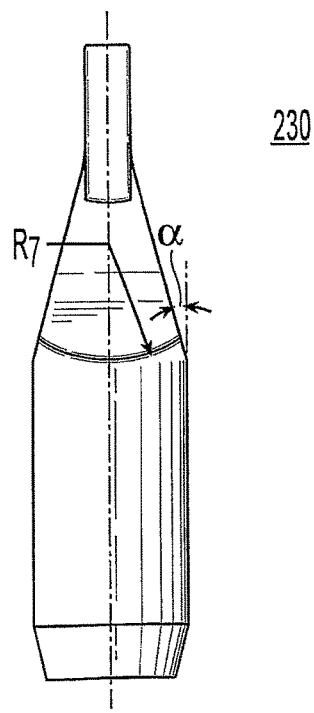
Figure 19:
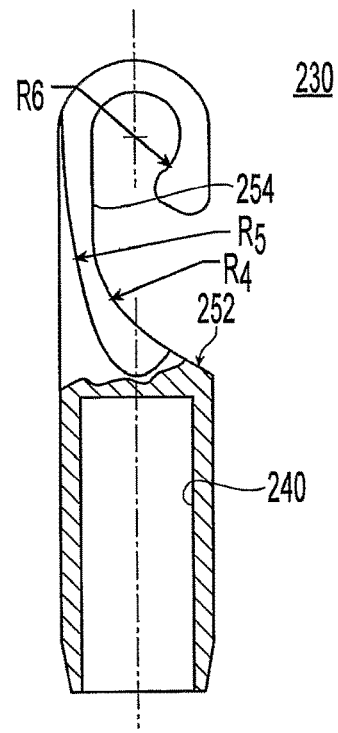
Figure 20:
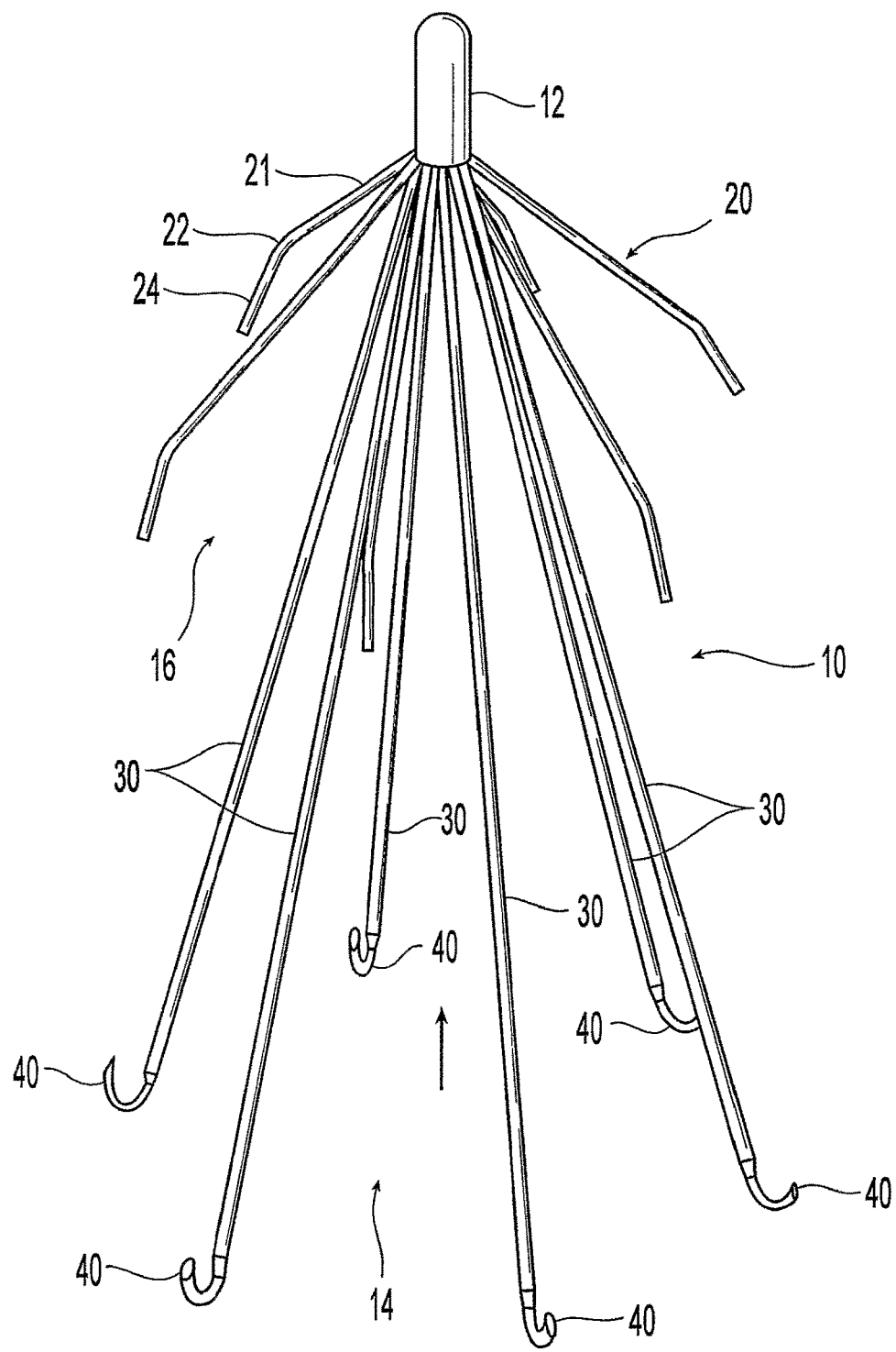
FIG. 20 is a side elevation view of a prior art expanded blood clot filter.
Figure 21:
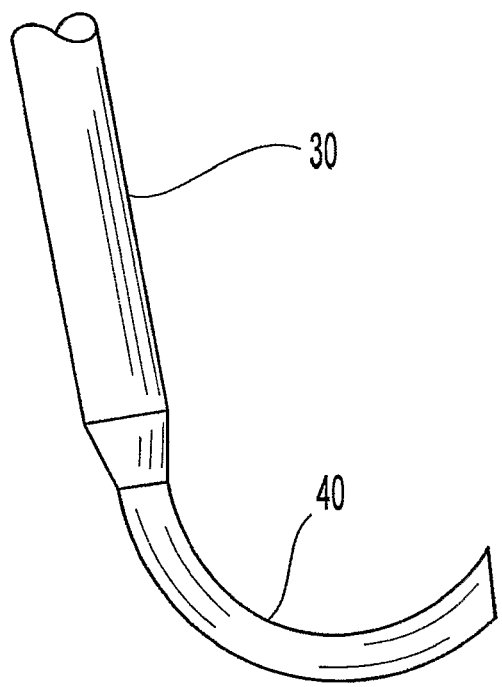
FIG. 21 is a side elevation view of a hook for use with the filter of FIG. 20.
Figure 22:
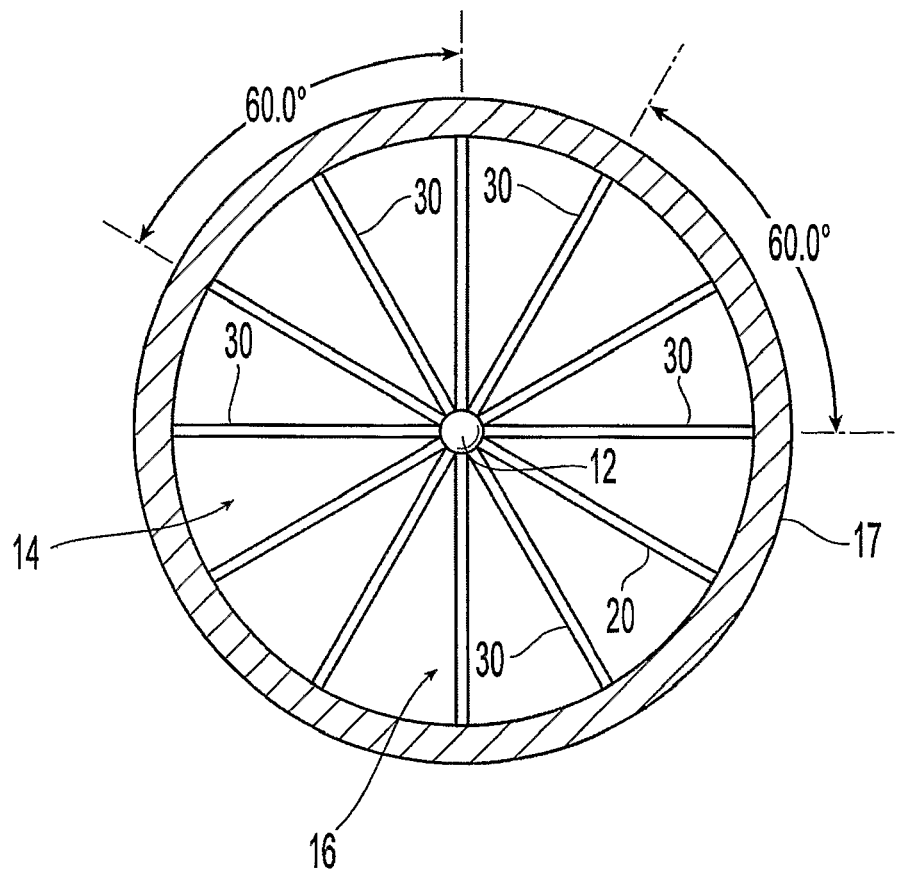
FIG. 22 is an end view of the filter of FIG. 20 in place in a blood vessel.

Referring to FIGS. 16-19, the retrieving hook 220 is configured to be easily captured by a snaring device used to retrieve the filter 200 from a subject. Referring to FIGS. 16 and 17, the retrieving hook 220 can be formed as a monolithic member 230 with the hub 210 or as a separate member joined to the hub 210 by a suitable technique, such as, for example, laser welding, plasma welding, brazing, welding, soldering, or bonding. In a preferred embodiment, the member 230 may be a machined billet member with a blind bore 240 formed through a portion of the hub 210. The hook portion 220 preferably includes ramped surfaces 250 and 260 that are believed to be advantageous in allowing the filter 200 to be retrieved without binding at the catheter opening due to an offset entry position of the filter 200. In other words, there may be circumstances during removal procedures where the axis 300 of the member 230 is not generally parallel or aligned with a longitudinal axis of the catheter retrieving device. In such cases, the greater the retention force, it is believed that the greater the likelihood of the hook being snagged on the catheter inlet opening thereby complicating the filter retrieval process. By virtue of the ramps 250 and 260, it is believed that binding or snagging is substantially reduced. In particular, as shown in FIGS. 18 and 19, the ramp 250 includes a radius of curvature $R_4$ coupled to a first flat portion 252 and a second flat portion 254. The flat portion 254 can be coupled to a hook portion 220 which has a radiused surface $R_6$. As shown in FIG. 18, the first flat portion 252 is preferably coupled to another radiused portion $R_7$.

Bio-active agents can be incorporated with the bio-resorbable covering material in the various embodiments. Such bio-active agents include (but are not limited to) pharmaceutic agents such as, for example, anti-proliferative/antimitotic agents including natural products such as vinca alkaloids (i.e. vinblastine, vincristine, and vinorelbine), paclitaxel, epipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

Although the preferred embodiments of the invention have been shown and described in relation to the filters of FIGS. 2 and 5, other filters can also be utilized such as, for example, commercially available filters that include a retainer as part of their overall design.

While the present invention has been disclosed with reference to certain preferred embodiments, numerous modifications, alterations, and changes to the described embodiments are possible without departing from the sphere and scope of the present invention. Accordingly, it is intended that the present invention not be limited to the described embodiments, but that it have the full scope defined by the language of the following claims, and equivalents thereof.

What is claimed is:

1. A filter to be placed in a blood vessel, the filter comprising:
   a) a plurality of appendages, each appendage having an anchor member with a distal end sharp tip;
   b) a bio-resorbable mass of material that encapsulates the distal end sharp tip, wherein when initially placed in a patient's vessel said mass of material has an outer surface that is smooth for enabling the mass of material to slide along the inside of the vessel;
   c) wherein when in use in said patient's vessel, the bio-resorbable mass of material that encapsulates the distal end sharp tip of at least one of the plurality of appendages resorbs after time and allows the distal end sharp tip to engage the vessel;
   d) a hub coupled to the plurality of appendages, the plurality of appendages further comprising a plurality of locator members that locate the filter with respect to a wall of the blood vessel;
   e) a plurality of anchor members coupled to the hub, at least one of the plurality of anchor members having a retainer configured to penetrate a wall of the blood vessel when the filter is disposed in the blood vessel, wherein
   f) a rounded bead shaped bio-resorbable mass of material that encompasses at least a portion of the retainer of the at least one of the plurality of anchor members;
   g) the retainer is held by the mass of bio-resorbable material in a first position wherein the rounded bead shaped mass of material is able to slide along the vessel wall, said retainer moving to a second position when the bio-resorbable material resorbs; and
   h) wherein the first and second positions have different curvatures for the retainer.

2. The filter of claim 1, wherein the bio-resorbable mass of material is coated by a water repellant coating.

3. The filter of claim 2, wherein the water repellant coating is activated by radiation to become at least partially porous.

4. The filter of claim 3, wherein the water repellant coating is activated by radiation having a wavelength of approximately 800 nm.

5. The filter of claim 1, wherein the anchor member has a hook shape in said second position.

6. A filter to be placed in a blood vessel, the filter comprising:
   a) a plurality of appendages, each appendage having an anchor member with a distal end sharp tip;
   b) a bio-resorbable mass of material that encapsulates the distal end sharp tip, wherein when initially placed in a patient's vessel said mass of material has an outer surface that is smooth for enabling the mass of material to slide along the inside of the vessel;
c) wherein when in use in said patient's vessel, the bio-resorbable mass of material that encapsulates the distal end sharp tip of at least one of the plurality of appendages resorbs after time and allows the distal end sharp tip to engage the vessel;
d) a hub disposed along a longitudinal axis, the hub being coupled to the plurality of appendages;
e) wherein the appendages are each coupled to the hub, each anchor member including a retainer spaced along the longitudinal axis from the hub at a first longitudinal distance, and radially spaced apart from the hub at a first longitudinal distance, and radially spaced from the longitudinal axis a first radial distance, each curved anchor member being configured to penetrate a wall of the blood vessel when the filter is disposed in the blood vessel; and
f) wherein the plurality of appendages comprise a plurality of locator members, each locator member including:
a first portion proximate the hub;
a second portion that extends from the first portion along a first axis;
a third portion that extends from the second portion along a second axis distinct from the first axis; and
g) the bio-resorbable mass of material encompasses at least a portion of the retainer of the at least one of the plurality of anchor members;
h) the retainer is held by the mass of bio-resorbable material in a first position, moving to a second position when the bio-resorbable material resorbs; and
i) wherein the first and second positions have different curvatures for the retainer.

7. The filter of claim 6, wherein:
the second portion extends from the first portion a first length along the first axis, which is oblique with respect to the longitudinal axis; and
the third portion extends a second length along the second axis, wherein the second length is greater than the first length, and the second axis is oblique with respect to the longitudinal axis.

8. The filter of claim 6, wherein the first portion of each of the plurality of locator members includes a curved portion defining a radius of curvature, the first portion forming a first angle with respect to the longitudinal axis.

9. The filter of claim 8, wherein the first axis defines a second angle with respect to the longitudinal axis, the second axis defines a third angle with respect to the longitudinal axis, the first angle being greater than each of the second and third angles.

10. A filter to be placed in a patient's blood vessel, the filter comprising:
a) a plurality of appendages, at least some of the appendages having an anchor member with a distal end sharp tip;
b) a rounded bead shaped bio-resorbable mass of material that encapsulates the distal end sharp tip, wherein said mass of material has an outer surface that is smooth for enabling the mass of material to slide along the inside of the vessel; and,
c) a hub disposed along a longitudinal axis, the hub being coupled to the plurality of appendages;
d) wherein the appendages are each coupled to the hub, each anchor member spaced along the longitudinal axis from the hub at a first longitudinal distance, and radially spaced from the longitudinal axis a first radial distance, each anchor member distal end sharp tip being configured to penetrate a wall of the blood vessel when the filter is disposed in the blood vessel; and
e) wherein when in use in the vessel, the bio-resorbable mass of material initially encapsulates the distal end sharp tip of at least one of the plurality of appendages and later resorbs after time and allows the distal end sharp tip to engage the vessel; and
f) wherein the plurality of appendages comprise a plurality of locator members, each locator member including:
a first portion proximate the hub;
a second portion that extends from the first portion along a first axis; and
a third portion that extends from the second portion along a second axis distinct from the first axis; and,
g) wherein each of the plurality of anchor members includes a first portion proximal the hub and a second portion distal the hub, each of the first and second portions of the anchor members being generally linear and disposed on distinct axes each oblique to the longitudinal axis, wherein the first portion of the anchor members is longer than the second portion of the anchor members and each of the plurality of anchor members is coupled to the second portion of the locator members.

11. The filter of claim 10, wherein each of the plurality of anchor members is offset in alignment with respect to the axis on which at least one portion of the corresponding, anchor member is aligned.

12. The filter of claim 10, wherein:
a) the first portion of each of the plurality of anchor members extends away from the longitudinal axis at a fourth angle;
b) the second portion of each of the plurality of anchor members extends away from the longitudinal axis at a fifth angle; and
c) the fourth angle is less than the fifth angle.

13. The filter of according to claim 10, wherein each distal end sharp tip of the plurality of appendages comprises a hook having a curved configuration in an operative condition and a generally linear configuration in a constrained condition.

14. The filter of claim 10, wherein the hub comprises a retrieving hook.

15. The filter of claim 10,
a) wherein the first portion includes a curved portion defining a radius of curvature of about 0.02 inches, the first portion extending to a point radially about 0.4 inches from the longitudinal axis and axially about 0.3 inches from the hub;
b) the second portion of each of the plurality of locator members extends to a point radially about 0.75 inches from the longitudinal axis and axially about 0.9 inches from the hub; and
c) wherein at least one hook of the plurality of anchor members includes a portion being radially about 0.75 from the longitudinal axis and axially about 1.3 inches from the hub, each of the plurality of anchor member includes a hook defining a radius of curvature of about 0.03 inches and having a tip portion defining an axial length of about 0.05 inches.

16. The filter of claim 10, wherein at least one of the plurality of locator members and the plurality of anchor members comprises at least one of a hook, a projection oblique to the locator member, a barb disposed on the locator member, or a tip having two barbs extending therefrom.

17. The filter of claim 10, wherein at least one of the plurality of locator members and the plurality of anchor members comprises a curved hook having a deformed configuration so as to be generally linear, the hook being covered by the bio-resorbable material to maintain the hook in the deformed configuration.

\* \* \* \* \*

UNITED STATES PATENT AND TRADEMARK OFFICE
CERTIFICATE OF CORRECTION

PATENT NO. : 10,368,972 B2
APPLICATION NO. : 15/247269
DATED : August 6, 2019
INVENTOR(S) : Alexander Germanovich Kashkarov and Andrzej J. Chanduszko Page 1 of 1

It is certified that error appears in the above-identified patent and that said Letters Patent is hereby corrected as shown below:

In the Specification

Column 7, Line 10, "potycaprolate" should be changed to "polycaprolate".

Column 8, Line 18, "returner" should be changed to "retainer".

Column 10, Line 25, the "ill" should be changed to "LJ1".

Column 10, Line 27, "LJI" should be changed to "LJ1".

Column 14, Line 5, "martensitk" should be changed to "martensitic".

In the Claims

Column 18, Line 37, "according to" should be deleted.

Signed and Sealed this
Seventeenth Day of September, 2019

Andrei Iancu
*Director of the United States Patent and Trademark Office*